US006518015B1

(12) United States Patent
Alizon et al.

(10) Patent No.: US 6,518,015 B1
(45) Date of Patent: *Feb. 11, 2003

(54) PEPTIDE COMPRISING THE SEQUENCE CAFRQVC AND METHODS USING IT

(75) Inventors: Marc Alizon, Paris (FR); Luc Montagnier, Le Plessis Robinson (FR); Denise G Guétard, Paris (FR); Francois Clavel, Rockville, MD (US); Pierre Sonigo, Paris (FR); Mireille Guyader, Paris (FR)

(73) Assignee: Institut Pasteur, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/862,029

(22) Filed: May 12, 2000

Related U.S. Application Data

(63) Continuation of application No. 08/774,736, filed on Jan. 2, 1997, now Pat. No. 6,261,762, which is a division of application No. 07/810,908, filed on Dec. 20, 1991, which is a division of application No. 07/752,368, filed on Sep. 3, 1991, now abandoned, which is a division of application No. 07/013,477, filed on Feb. 11, 1987, now Pat. No. 5,079,342, which is a division of application No. 07/003,764, filed on Jan. 16, 1987, now Pat. No. 5,051,496, which is a continuation-in-part of application No. 06/933,184, filed on Nov. 21, 1986, now abandoned, which is a continuation-in-part of application No. 06/916,080, filed on Oct. 6, 1986, now abandoned, which is a continuation-in-part of application No. 06/835,228, filed on Mar. 3, 1986, now Pat. No. 4,839,288.

(30) Foreign Application Priority Data

| Jan. 22, 1986 | (FR) | 86 00911 |
| Feb. 6, 1986 | (FR) | 86 01635 |
| Feb. 13, 1986 | (FR) | 86 01985 |
| Mar. 18, 1986 | (FR) | 86 03881 |
| Mar. 24, 1986 | (FR) | 86 04215 |

(51) Int. Cl.$^7$ ............................................... C12Q 1/70
(52) U.S. Cl. ........................... 435/5; 435/7.1; 435/974; 435/975; 436/518; 530/324; 530/325; 530/326; 530/328; 530/810
(58) Field of Search .................... 435/7.1, 974, 975; 436/518; 530/324, 325, 326, 328, 810

(56) References Cited

U.S. PATENT DOCUMENTS

| 4,629,783 A | 12/1986 | Cosand | 530/326 |
| 4,839,288 A | 6/1989 | Montagnier et al. | 435/235 |
| 5,079,342 A | 1/1992 | Alizon et al. | 530/324 |
| 5,480,966 A | 1/1996 | Sommé et al. | 530/324 |
| 5,670,309 A | 9/1997 | Norrby et al. | 435/5 |
| 5,721,095 A | 2/1998 | Chan et al. | 435/5 |
| 6,261,762 B1 * | 7/2001 | Alizon et al. | 435/5 |

FOREIGN PATENT DOCUMENTS

| EP | 0 316 695 B1 | 3/1993 |
| WO | WO 85/04897 | 11/1985 |

OTHER PUBLICATIONS

Allan et al., "Major Glycoprotein Antigens That Induce Antibodies in AIDS Patients Are Encoded by HTVL–III," Science 228:1091–94 (1985).

Barin et al., "Serological Evidnece For Virus Related to Simian T–lymphotropic Retrovirus III in Residents of West Africa," The Lancet 2:1387–1389 (1985).

Chang et al., "Detection of Antibodies to Human T–Cell Lymphotropic Virus–III (HTLV–III) with an Immunoassay Employing a Recombinant *Escherichia coli*–Derived viral Antigenic Peptide," bio/Technology 3:905–909 (1985).

Clavel et al., "Isolation of a New Human Retrovirus from West African Patients with AIDS," Science 233:343–346 (1986).

Clavel et al., "LAV Type II: A Second Retrovirus Associated with AIDS in West Africa," C.R. Acad. Sci. Paris, Series III 302:485–488 (1986).

Clavel et al., "Molecular cloning and polymorphism of the human immunodeficiency virus type 2," Nature 324:691–695 (1986).

Daniel et al., "Isolation of T–Cell Tropic HTLV–III–like Retrovirus from Macaques," Science 228:1201–1204 (1985).

Damell et al., "The Molecules in Cells: Proteins," Molecular Cell Biology, pp. 53–57 (1986).

Fields et al., "Human Immunodeficiency Viruses and Their Replication," Virology 2:1913–16 (1996 3$^{rd}$ ed).

Gallo et al., "HIV/HTLV gene nomenclature," Nature 333:504 (1988).

Gao et al., "Genetic Diversity of Human Immunodeficiency Virus Type 2: Evidence for Distinct Sequence Subtypes with Differences in Virus Biology," J. Virol. 68(11):7433–7447 (1994).

Goodenow et al., "HIV–1 Isolates Are Rapidly Evolving Quasispecies: Evidence for Viral Mixtures and Preferred Nucleotides Substitutions," J. Acquir. Immun. Defic. Syndr. 2:344–352 (1989).

Kanki et al., "Isolation of T–lymphotropic Retrovirus Related to HTLV–III/LAV from Wild–Caught African Green Monkeys," Science 230:951–954 (1985).

Kanki et al., "Serologic Identification and Characterization of a Macaque T–lymphotropic Retrovirus Closely Related to HTLV–III," Science 228:1199–1201 (1985).

Klatzmann et al., "T–lymphocyte T4 Molecule Behaves As The Receptor for Human Retrovirus LAV," Nature 312:767–768 (1984).

(List continued on next page.)

Primary Examiner—Jeffrey Stucker
(74) Attorney, Agent, or Firm—Finnegan, Henderson, Farabow, Garrett & Dunner, L.L.P.

(57) ABSTRACT

This invention includes a peptide comprising the sequence CAFRQVC and an antigenic composition using the same. It also includes an in vitro method of detecting HIV-1 and HIV-2 antibodies in a sample using the peptide, and a kit for carrying out the method.

16 Claims, 5 Drawing Sheets

OTHER PUBLICATIONS

Laurence, J., "Editorial Update: HIV–1 Gene Nomenclature," AIDS Res. Hum. Retroviruses 4:vii–viii (1988).

Mitsuya et al., "Protection of T Cells Against Infectivity and Cytopathic Effect of HTLV–III In Vitro," Retroviruses in Human Lymphoma/Leukemia, Proceedings of the 15$^{th}$ International Symposium of The Princess Takamatsu Cancer Research Fund, Tokyo, 1984, 277–288 (1985).

Sandstrom et al., "Antiviral Therapy in AIDS Clinical Pharmacological Properties and Therapeutic Experience to Date," Drugs 34:372–390 (1987).

* cited by examiner

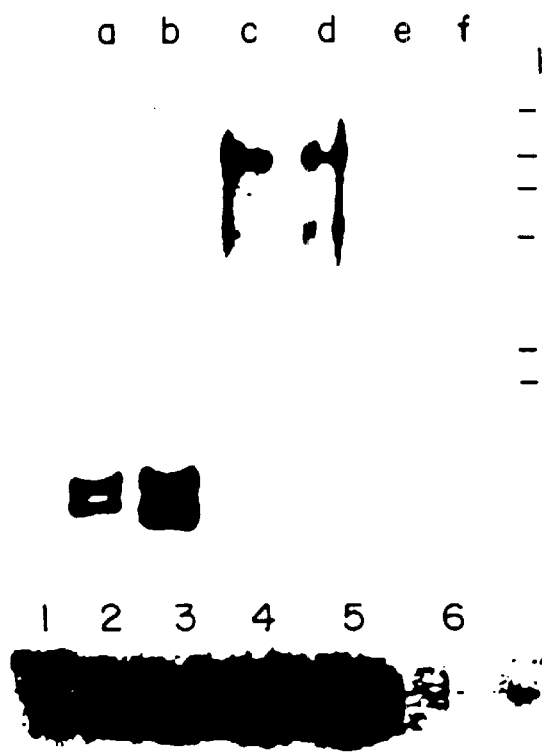
FIG.2A
FIG.2C
FIG.2B
FIG.2D

PEPTIDE COMPRISING THE SEQUENCE CAFRQVC AND METHODS USING IT

This is a continuation of application Ser. No. 08/774,736, filed Jan. 2, 1997 now U.S. Pat. No. 6,261,762 which is a division of 07/810,908, filed Dec. 20, 1991, which is a division of 07/752,368, filed Sep. 3, 1991 now abandoned, which is a division of 07/013,477, filed Feb. 11, 1987 now U.S. Pat. No. 5,079,342, which is a division of 07/003,764, filed Jan. 16, 1981 now U.S. Pat. No. 5,051,496, which is a CIP of 06/933,184, filed Nov. 21, 1986 now abandoned, which is a CIP of 06/916,080, filed Oct. 6, 1986 now abandoned, which is a CIP of 06/835,228, filed Mar. 3, 1986 now U.S. Pat. No. 4,839,288, which is a CIP based on FR 86 00911, filed on Jan. 22, 1986, based on FR 86 01635, filed on Feb. 6, 1986, based on FR 86 01985, filed Feb. 13, 1986, based on FR 86 03881, filed on Mar. 18, 1986, based on FR 86 04215, filed on Mar. 24 1986, incorporated herein by reference.

BACKGROUND OF THE INVENTION

The invention relates to cloned DNA sequences analogous to the genomic RNA of a virus known as Lymphadenopathy-Associated Virus II ("LAV-II"), a process for the preparation of these cloned DNA sequences, and their use as probes in diagnostic kits. In one embodiment, the invention relates to a cloned DNA sequence analogous to the entire genomic RNA of HIV-2 and its use as a probe. The invention also relates to polypeptides with amino acid sequences encoded by these cloned DNA sequences and the use of these polypeptides in diagnostic kits.

According to recently adopted nomenclature, as reported in Nature, May 1986, a substantially-identical group of retroviruses which has been identified as one causative agent of AIDS are now referred to as Human Immunodeficiency Viruses I (HIV-1). This previously-described group of retroviruses includes Lymphadenopathy-Associated Virus I (LAV-I), Human T-cell Lymphotropic Virus-III (HTLV-III), and AIDS-Related Virus (ARV).

Lymphadenopathy-Associated Virus II has been described in U.S. application Ser. No. 835,228, which was filed Mar. 3, 1986, and is specifically incorporated herein by reference. Because LAV-II is a second, distinct causative agent of AIDS, LAV-II properly is classifiable as a Human Immunodeficiency Virus II (HIV-2). Therefore, "LAV-II" as used hereinafter describes a particular genus of HIV-2 isolates.

While HIV-2 is related to HIV-1 by its morphology, its tropism and its in vitro cytopathic effect on CD4 (T4) positive cell lines and lymphocytes, HIV-2 differs from previously described human retroviruses known to be responsible for AIDS. Moreover, the proteins of HIV-1 and 2 have different sizes and their serological cross-reactivity is restricted mostly to the major core protein, as the envelope glycoproteins of HIV-2 are not immune precipitated by HIV-1-positive sera except in some cases where very faint cross-reactivity can be detected. Since a significant proportion of the HIV infected patients lack antibodies to the major core protein of their infecting virus, it is important to include antigens to both HIV-1 and HIV-2 in an effective serum test for the diagnosis of the infection by these viruses.

HIV-2 was first discovered in the course of serological research on patients native to Guinea-Bissau who exhibited clinical and immunological symptoms of AIDS and from whom sero-negative or weakly sero-positive reactions to tests using an HIV-1 lysate were obtained. Further clinical studies on these patients isolated viruses which were subsequently named "LAV-II."

One LAV-II isolate, subsequently referred to as LAV-II MIR, was deposited at the Collection Nationale des Cultures de Micro-Organismes (CNCM) at the Institut Pasteur in Paris, France on Dec. 19, 1985 under Accession No. I-502 and has also been deposited at the British ECA CC under No. 87.001.001 on Jan. 9, 1987. A second LAV-II isolate was deposited at CNCM on Feb. 21, 1986 under Accession No. I-532 and has also been deposited at the British ECA CC under No. 87.001.002 on Jan. 9, 1987. This second isolate has been subsequently referred to as LAV-II ROD. Other isolates deposited at the CNCM on Dec. 19, 1986 are HIV-2 IRMO (No. I-642) and HIV-2 EHO (No. I-643). Several additional isolates have been obtained from West African patients, some of whom have AIDS, others with AIDS-related conditions and others with no AIDS symptoms. All of these viruses have been isolated on normal human lymphocyte cultures and some of them were thereafter propagated on lymphoid tumor cell lines such as CEM and MOLT.

Due to the sero-negative or weak sero-positive results obtained when using kits designed to identify HIV-1 infections in the diagnosis of these new patients with HIV-2 disease, it has been necessary to devise a new diagnostic kit capable of detecting HIV-2 infection, either by itself or in combination with an HIV-1 infection. The present inventors have, through the development of cloned DNA sequences analogous to at least a portion of the genomic RNA of LAV-II ROD viruses, created the materials necessary for the development of such kits.

SUMMARY OF THE INVENTION

As noted previously, the present invention relates to the cloned nucleotide sequences homologous or identical to at least a portion of the genomic RNA of HIV-2 viruses and to polypeptides encoded by the same. The present invention also relates to kits capable of diagnosing an HIV-2 infection.

Thus, a main object of the present invention is to provide a kit capable of diagnosing an infection caused by the HIV-2 virus. This kit may operate by detecting at least a portion of the RNA genome of the HIV-2 virus or the provirus present in the infected cells through hybridization with a DNA probe or it may operate through the immunodiagnostic detection of polypeptides unique to the HIV-2 virus.

Additional objects and advantages of the present invention will be set forth in part in the description which follows, or may be learned from practice of the invention. The objects and advantages may be realized and attained by means of the instrumentalities and combinations particularly pointed out in the appended claims.

To achieve these objects and in accordance with the purposes of the present invention, cloned DNA sequences related to the entire genomic RNA of the LAV-II virus are set forth. These sequences are analogous specifically to the entire genome of the LAV-II ROD strain.

To further achieve the objects and in accordance with the purposes of the present invention, a kit capable of diagnosing an HIV-2 infection is described. This kit, in one embodiment, contains the cloned DNA sequences of this invention which are capable of hybridizing to viral RNA or analogous DNA sequences to indicate the presence of an HIV-2 infection. Different diagnostic techniques can be used which include, but are not limited to: (1) Southern blot procedures to identify viral DNA which may or may not be digested with restriction enzymes; (2) Northern blot techniques to identify viral RNA extracted from cells; and (3) dot blot techniques, i.e., direct filtration of the sample through an ad hoc membrane such as nitrocellulose or nylon without previous separation on agarose gel. Suitable material for dot blot technique could be obtained from body fluids including, but not limited to, serum and plasma, supernatants from culture cells, or cytoplasmic extracts obtained after cell lysis and removal of membranes and nuclei of the cells by ultra-centrifugation as accomplished in the "CYTODOT" procedure as described in a booklet published by Schleicher and Schull.

In an alternate embodiment, the kit contains the polypeptides created using these cloned DNA sequences. These polypeptides are capable of reacting with antibodies to the HIV-2 virus present in sera of infected individuals, thus yielding an immunodiagnostic complex.

To further achieve the objects of the invention, a vaccinating agent is provided which comprises at least one peptide selected from the polypeptide expression products of the viral DNA in admixture with suitable carriers, adjuvents stabilizers.

It is understood that both the foregoing general description and the following detailed description are exemplary and explanatory only and are not restrictive of the invention as claimed. The accompanying drawings, which are incorporated in and constitute a part of the specification, illustrate one embodiment of the invention and, together with the description, serve to explain the principles of the invention.

BRIEF DESCRIPTION OF THE DRAWINGS

FIG. 1 generally depicts the nucleotide sequence of a cloned complementary DNA (cDNA) to the genomic RNA of HIV-2. In FIG. 1B, the symbols B, H, Ps and Pv refer to the restriction sites BamHI, HindIII, PstI and PvuII, respectively.

FIG. 2 generally depicts the HIV-2 specificity of the E2 clone. FIGS. 2A and B specifically depict a Southern blot of DNA extracted from CEM cells infected with the following isolates: HIV-2$_{ROD}$ (a,c), HIV-2$_{DUL}$ (b,d), and HIV-1$_{BRU}$ (e,f). DNA in lanes a, b, f was Pst I digested; in c, d, e DNA was undigested. FIGS. 2C and D specifically depict dot blot hybridization of pelleted virions from CEM cells infected by the HIV-1$_{BRU}$ (1), Simian Immunodeficiency Virus (SIV) isolate Mm 142-83 (3), HIV-2$_{DUL}$ (4), HIV-2$_{ROD}$ (5), and HIV-1$_{ELI}$ (6). Dot 2 is a pellet from an equivalent volume of supernatant from uninfected CEM. Thus, FIGS. 2A and C depicts hybridization with the HIV-2 cDNA (E2) and FIGS. 2B and D depicts hybridization to an HIV-1 probe consisting of a 9 Kb SacI insert from HIV-1 BRU(clone lambda J 19).

FIG. 3 generally depicts a restriction map of the HIV-2 ROD genome and its homology to HIV-1. In FIG. 3A, the open boxes represent viral sequences, the LTR are filled, and the dotted boxes represent cellular flanking sequences (not mapped). Only some characteristic restriction enzyme sites are indicated. λROD 27 and ROD 35 are derived from integrated proviruses while λROD 4 is derived from a circular viral DNA. The portion of the lambda clones that hybridzes to the cDNA E2 is indicated below the maps. A restriction map of the λROD isolate was reconstructed from these three lambda clones. In this map, the restriction sites are identified as follows: B: BamHI; E: EcoRI; H: HindIII; K: KpnI; Ps: PstI; Pv: PvuII; S: SacI; X: XbaI. R and L are the right and left BamHI arms of the lambda L47.1 vector.

FIG. 4 generally depicts the restriction map polymorphism in different HIV-2 isolates and shows comparison of HIV-2 to SIV.

DETAILED DESCRIPTION OF THE PREFERRED EMBODIMENTS

Reference will now be made in detail to the presently preferred embodiments of the invention, which, together with the following examples, serve to explain the principles of the invention.

Figures 1A, 1B:
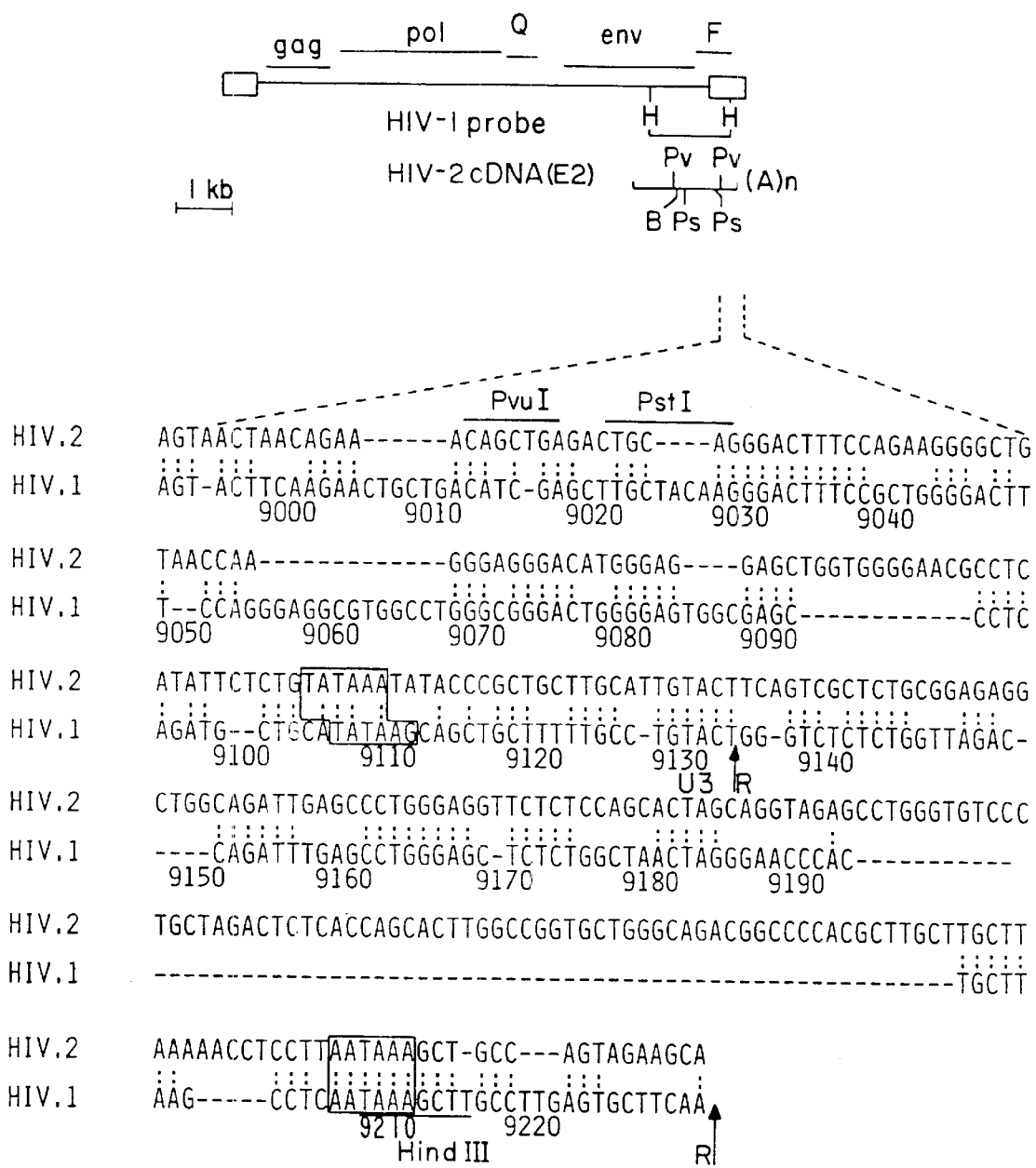
FIG. 1A depicts the genetic organization of HIV-1, position of the HIV-1 HindIII fragment used as a probe to screen the cDNA library, and restriction map of the HIV-2 cDNA clone, E2.
FIG. 1B depicts the nucleotide sequence of the 3' end of HIV-2. The corresponding region of the HIV-1 LTR was aligned using the Wilbur and Lipman algorithm (window: 10; K-tuple: 7; gap penalty: 3) as described by Wilbur and Lipman in Proc. Natl. Acad. Sci. USA 80: 726–730 (1983), specifically incorporated herein by reference. The U3-R junction in HIV-1 is indicated and the poly A addition signal and potential TATA promoter regions are boxed.

The genetic structure of the HIV-2 virus has been analyzed by molecular cloning according to the method set forth herein and in the Examples. A restriction map of the genome of this virus is included in FIG. 4. In addition, the partial sequence of a cDNA complementary to the genomic RNA of the virus has been determined. This cDNA sequence information is included in FIG. 1.

Also contained herein is data describing the molecular cloning of the complete 9.5 kb genome of HIV-2, data describing the observation of restriction map polymorphism between different isolates, and an analysis of the relationship between HIV-2 and other human and simian retroviruses. From the totality of these data, diagnostic probes can be discerned and prepared.

Generally, to practice one embodiment of the present invention, a series of filter hybridizations of the HIV-2 RNA genome with probes derived from the complete cloned HIV-1 genome and from the ca and Dol genes were conducted. These hybridizations yielded only extremely weak signals even in conditions of very low stringency of hybrization and washing. Thus, it was found to be difficult to assess the amount of HIV-2 viral and proviral DNA in infected cells by Southern blot techniques.

Therefore, a complementary DNA (cDNA) to the HIV-2 genomic RNA initially was cloned in order to provide a specific hybridization probe. To construct this cDNA, an oligo (dT) primed cDNA first-strand was made in a detergent-activated endogenous reaction using HIV-2 reverse transcriptase with virions purified from supernatants of infected CEM cells. The CEM cell line is a lymphoblastoid CD4+ cell line described by G. E. Foley et al. in Cancer 18: 522–529 (1965), specifically incorporated herein by reference. The CEM cells used were infected with the isolate ROD and were continuously producing high amounts of HIV-2.

After second-strand synthesis, the cDNAs were inserted into the M 13 tg 130 bacteriophage vector. A collection of $10^4$ M13 recombinant phages was obtained and screened in situ with an HIV-1 probe spanning 1.5 kb. of the 3' end of the LAV$_{BRU}$ isolate (depicted in FIG. 1A). Some 50 positive plaques were detected, purified, and characterized by end sequencing and cross-hybridizing the inserts. This procedure is described in more detail in Example 1 and in FIG. 1.

The different clones were found to be complementary to the 3' end of a polyadenylated RNA having the AATAAA signal about 20 nucleotides upstream of the poly A tail, as found in the long terminal repeat (LTR) of HIV-1. The LTR region of HIV-1 has been described by S. Wain Hobson et al. in Cell 40: 9–17 (1985), specifically incorporated herein by reference. The portion of the HIV-2 LTR that was sequenced was related only distantly to the homologous domain in HIV-1 as demonstrated in FIG. 1B. Indeed, only about 50% of the nucleotides could be aligned and about a hundred insertions/deletions need to be introduced. In comparison, the homology of the corresponding domains in HIV-1 isolates from USA and Africa is greater than 95% and no insertions or deletions are seen.

The largest insert of this group of M13 clones was a 2 kb. clone designated E2. Clone E2 was used as a probe to demonstrate its HIV-2 specificity in a series of filter hybridization experiments. Firstly, this probe could detect the genomic RNA of HIV-2 but not HIV-1 in stringent conditions as shown in FIG. 2, C and D. Secondly, positive signals were detected in Southern blots of DNA from cells infected with the ROD isolate as well as other isolates of HIV-2 as shown in FIG. 2, A and FIG. 4, A. No signal was detected with DNA from uninfected cells or HIV-1 infected cells, confirming the exogenous nature of HIV-2. In undigested DNA from HIV-2 infected cells, an approximately 10 kb. species, probably corresponding to linear unintegrated viral DNA, was principally detected along with a species with an apparent size of 6 kb., likely to be the circular form of the viral DNA. Conversely, rehybridization of the same filter with an HIV-1 probe under stringent conditions showed hybridization to HIV-1 infected cells only as depicted in FIG. 2, B.

To isolate the remainder of the genome of HIV-2, a genomic library in lambda phage L47.1 was constructed. Lambda phage L47.1 has been described by W. A. M. Loenen et al. in Gene 10: 249–259 (1980), specifically incorporated herein by reference. The genomic library was constructed with a partial Sau3AI restriction digest of the DNA from the CEM cell line infected with HIV-2$_{ROD}$.

About $2\times10^6$ recombinant plaques were screened in situ with labelled insert from the E2 cDNA clone. Ten recombinant phages were detected and plaque purified. Of these phages, three were characterized by restriction mapping and Southern blot hybridization with the E2 insert and probes from its 3' end (LTR) or 5' end (envelope), as well as with HIV-1 subgenomic probes. In this instance, HIV-1 probes were used under non-stringent conditions.

Figure 3A:
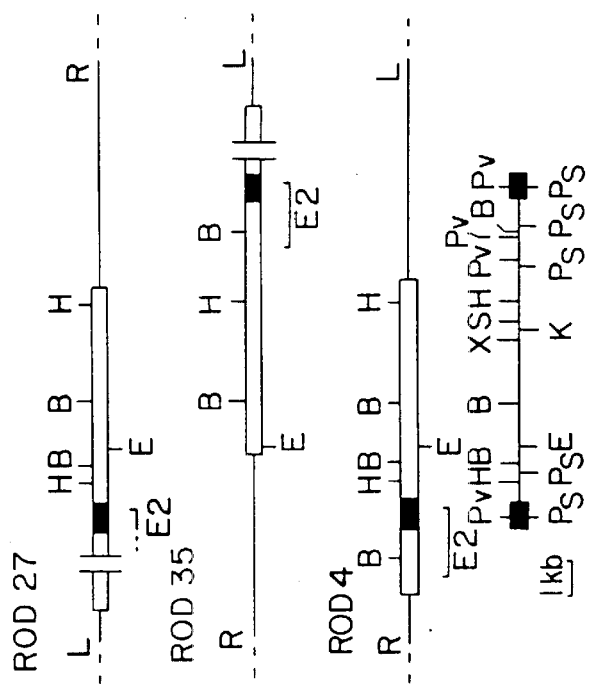
FIG. 3A specifically depicts the organization of three recombinant phage lambda clones, ROD 4, ROD 27, and ROD 35.
Figure 3B:
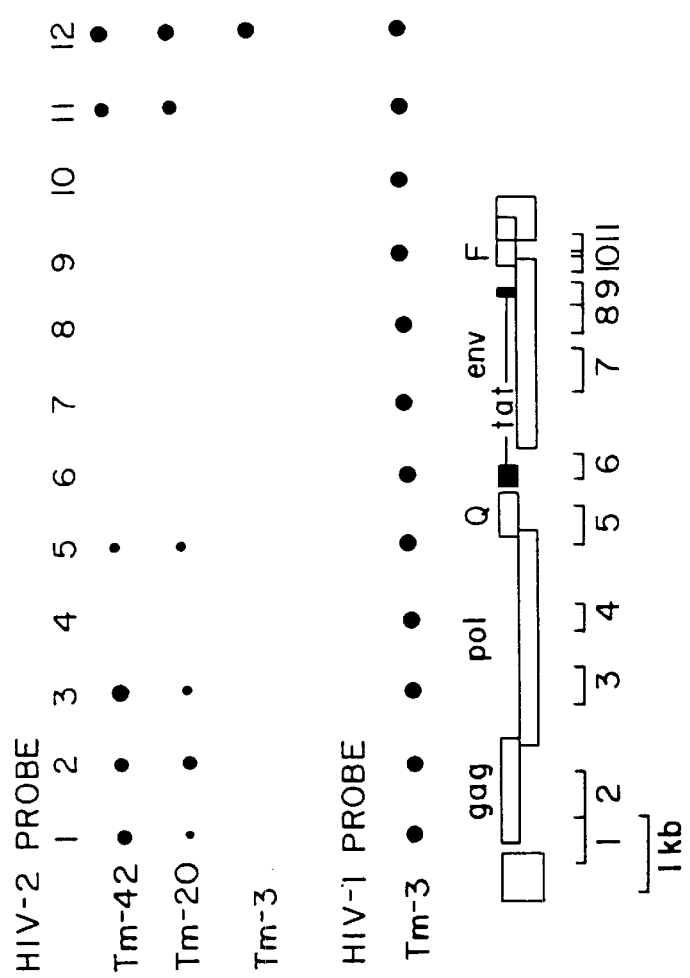
FIG. 3B specifically depicts dots 1–11 which correspond to the single-stranded DNA form of M13 subclones from the HIV-1$_{BRU}$ cloned genome (λJ19). Their size and position on the HIV-1 genome, determined by sequencing is shown below the figure. Dot 12 is a control containing lambda phage DNA. The dot-blot was hybridized in low stringency conditions as described in Example 1 with the complete lambda λROD 4 clone as a probe, and successively washed in 2×SSC, 0.1% SDS at 25° C. (Tm−42° C.),1×SSC, 0.1% SDS at 60° C. (Tm −20° C.), and 0.1×SSC, 0.1% SDS at 60° C. (Tm −3° C.) and exposed overnight. A duplicate dot blot was hybridized and washed in stringent conditions (as described in Example 2) with the labelled lambda J19 clone carrying the complete HIV-1$_{BRU}$ genome. HIV-1 and HIV-2 probes were labelled the same specific activity ($10^8$ cpm/g.).

A clone carrying a 9.5 kb. insert and derived from a circular viral DNA was identified as containing the complete genome and designated λROD 4. Two other clones, λROD 27 and λROD 35 were derived from integrated proviruses and found to carry an LTR and cellular flanking sequences and a portion of the viral coding sequences as shown in FIG. 3, A.

Fragments of the lambda clones were subcloned into a plasmid vector p UC 18.

Plasmid pROD 27-5' is derived from λROD 27 and contains the 5' 2Kb of the HIV-2 genome and cellular flanking sequences (5' LTR and 5' viral coding sequences to the EcoRI site)

Plasmid p ROD 4–8 is dervied from λROD 4 and contains the about 5 Kb HindIII fragment that is the central part of the HIV-2 genome.

Plasmid pROD 27-5' and p ROD 4.8 inserts overlap.

Plasmid pROD 4.7 contains a HindIII 1.8 Kb fragment from λROD 4. This fragment is located 3' to the fragment subcloned into pROD 4.8 and contains about 0.8 Kb of viral coding sequences and the part of the lambda phage (λL47.1) left arm located between the BamHI and HindIII cloning sites.

Plasmid pROD 35 contains all the HIV-2 coding sequences 3' to the EcoRI site, the 3' LTR and about 4 Kb of cellular flanking sequences.

Figure 5:
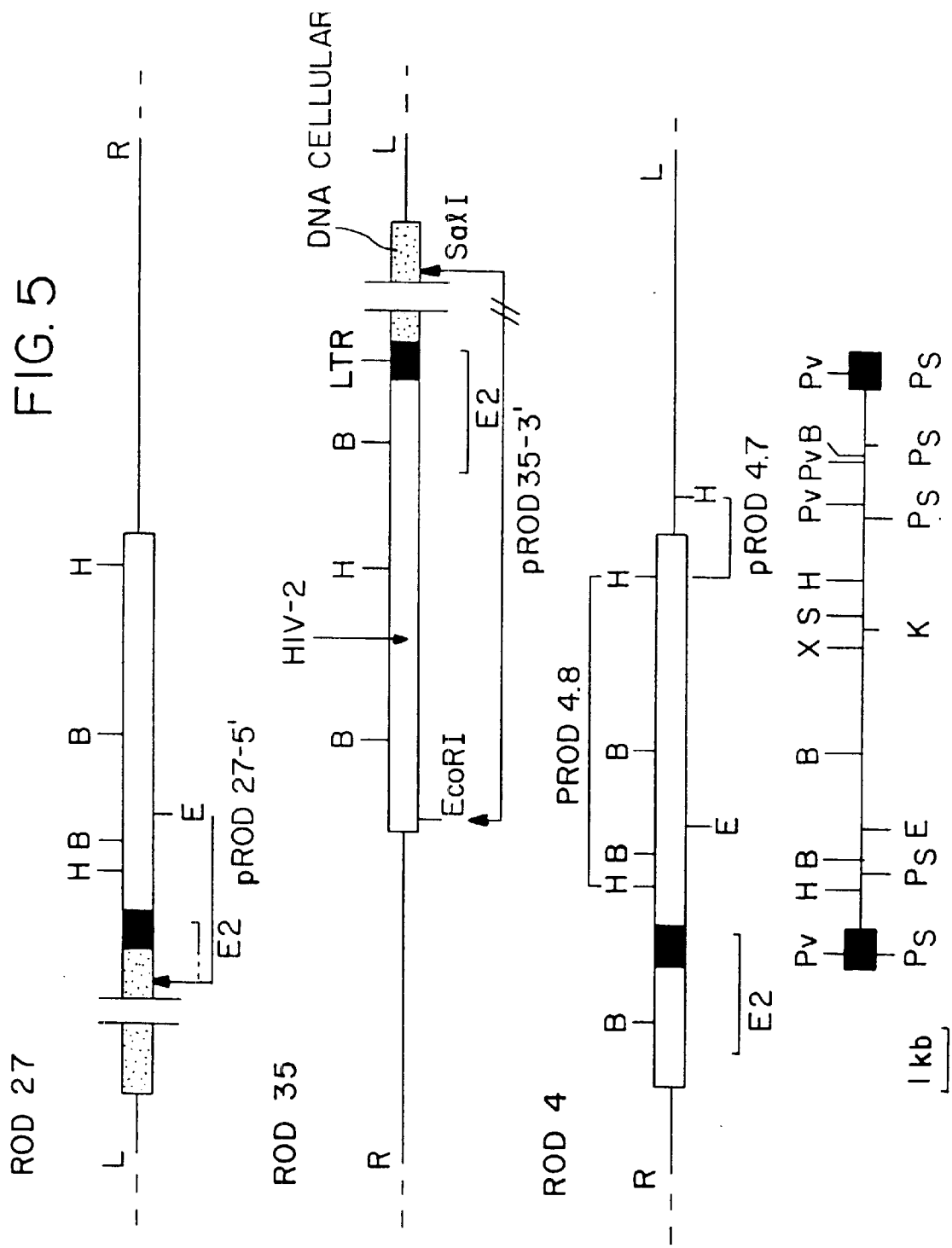
FIG. 5 depicts the position of derived plasmids from λROD 27, λROD 35 and λROD 4.

Plasmid pROD 27-5' and pROD 35 in *E. coli* strain HB 101 are deposited respectively under No. 1-626 and 1-633 at the CNCM, and have also been deposited at the NCIB (British Collection). These plasmids are depicted in FIG. 5. Plasmids pROD 4–7 and pROD 4–8 in *E. coli* strain TGI are deposited respectively under No. 1-627 and 1-628 at the CNCM.

To reconstitute the complete HIV-2 ROD genome, pROD 35 is linearized with EcoRI and the EcoRI insert of pROD 27-5' is ligated in the correct orientation into this site.

The relationship of HIV-2 to other human and simian retroviruses was surmised from hybridization experiments. The relative homology of the different regions of the HIV-1and 2 genomes was determined by hybridization of fragments of the cloned HIV-1 genome with the labelled λROD 4 expected to contain the complete HIV-2 genome (FIG. 3, B). Even in very low stringency conditions (Tm–42° C.), the hybridization of HIV-1 and 2 was restricted to a fraction of their genomes, principally the qaq gene (dots 1 and 2), the reverse transcriptase domain in pol (dot 3), the end of pol and the Q (or sor) genes (dot 5) and the F gene (or 3' orf) and 3' LTR (dot 11). The HIV-1 fragment used to detect the HIV-2 cDNA clones contained the dot 11 subclone, which hybridized well to HIV-2 under non-stringent conditions.

Only the signal from dot 5 persisted after stringent washing. The envelope gene, the region of the tat gene and a part of pol thus seemed very divergent. These data, along with the LTR sequence obtained (FIG. 1, B), indicated that HIV-2 is not an envelope variant of HIV-1, as are African isolates from Zaire described by Alizon et al., *Cell* 40: 63–74 (1986).

It was observed that HIV-2 is related more closely to the Simian Immunodeficiency Virus (SIV) than it is to HIV-1. This correlation has been described by F. Clavel et al. in C. R. Acad. Sci. (Paris) 302: 485–488 (1986) and F. Clavel et al. in Science 233: 343–346 (1986), both of which are specifically incorporated herein by reference. Simian Immunodeficiency Virus (also designated Simian T-cell Lymphotropic Virus Type 3, STLV-3) is a retrovirus first isolated from captive macaques with an AIDS-like disease in the USA. This simian virus has been described by M.D. Daniel et al. in Science 228: 1201–1204 (1985), specifically incorporated herein by reference.

All the SIV proteins, including the envelope, are immune precipitated by sera from HIV-2 infected patients, whereas the serological cross-reactivity of HIV-1 to 2 is restricted to the core proteins. However SIV and HIV-2 can be distinguished by slight differences in the apparent molecular weight of their proteins.

In terms of nucleotide sequence, it also appears that HIV-2 is closely related to SIV. The genomic RNA of SIV can be detected in stringent conditions as shown in FIG. 2, C by HIV-2 probes corresponding to the LTR and 3' end of the genome (E2) or to the qaq or pol genes. Under the same conditions, HIV-1 derived probes do not detect the SIV genome as shown in FIG. 2, D.

In Southern blots of DNA from SIV-infected cells, a restriction pattern clearly different from HIV-2$_{ROD}$ and other isolates is seen. All the bands persist after a stringent washing, even though the signal is considerably weakened, indicating a sequence homology throughout the genomes of HIV-2 and SIV. It has recently been shown that baboons and macaques could be infected experimentally by HIV-2, thereby providing an interesting animal model for the study of the HIV infection and its preventive therapy. Indeed, attempts to infect non-human primates with HIV-1 have been successful only in chimpanzees, which are not a convenient model.

Figure 4A:
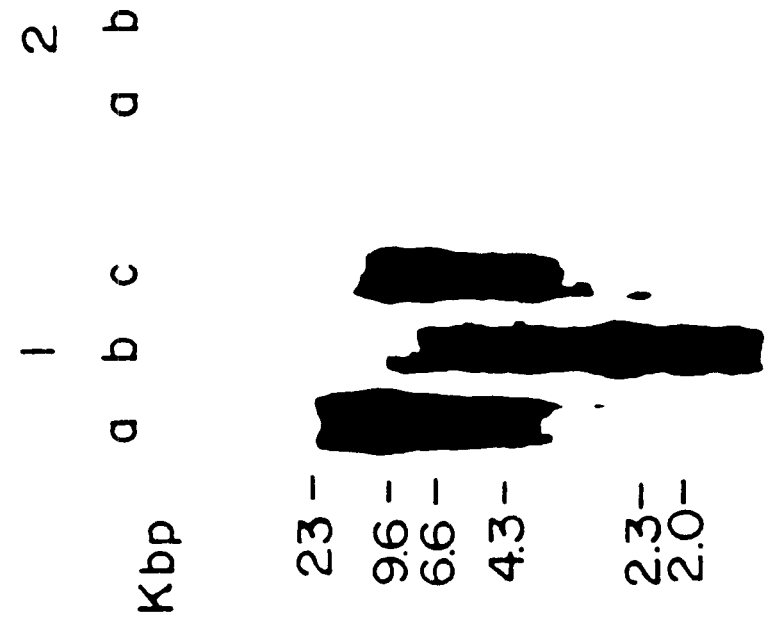
FIG. 4A specifically depicts DNA (20 ug. per lane) from CEM cells infected by the isolate HIV-2$_{DUL}$ (panel 1) or peripheral blood lymphocytes (PBL) infected by the isolates HIV-2$_{GOM}$ (panel 2) and HIV-2$_{MIR}$ (panel 3) digested with: EcoRI (a), PstI (b), and HindIII (c). Much less viral DNA was obtained with HIV-2 isolates propagated on PBL. Hybridization and washing were in stringent conditions, as described in Example 2, with 106 cpm/ml. of each of the E2 insert (cDNA) and the 5 kb. HindIII fragment of λROD 4, labelled to $10^9$ cpm/ug.
Figure 4B:
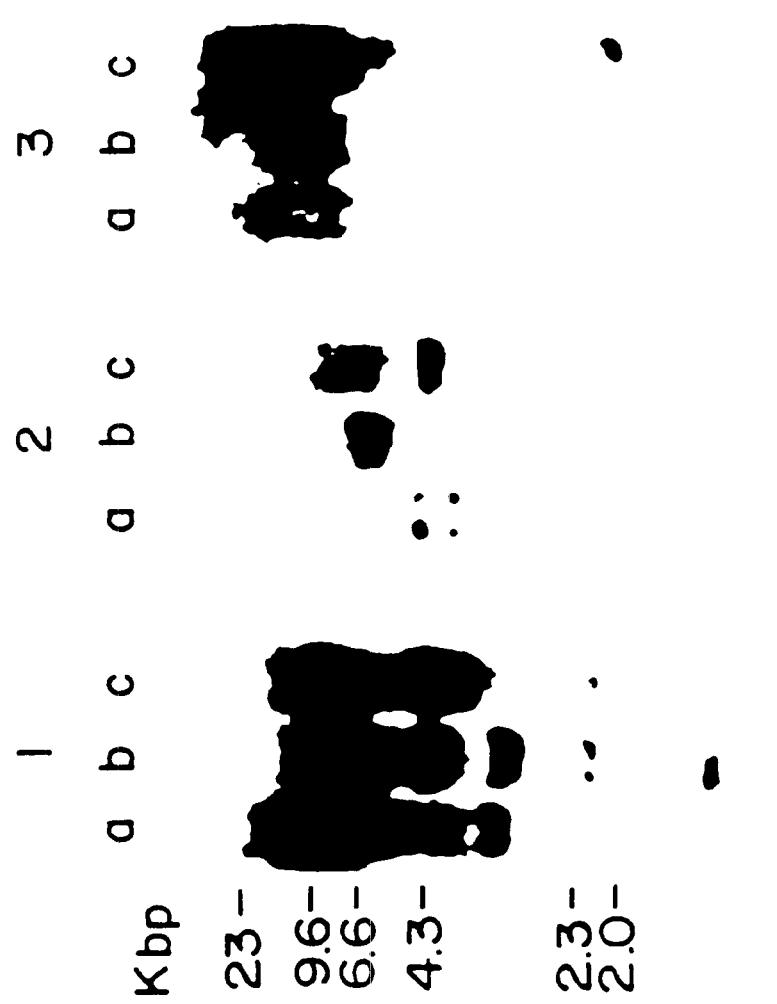
FIG. 4B specifically depicts DNA from HUT 78 (a human T lymphoid cell line) cells infected with STLV3 MAC isolate Mm 142–83. The same amounts of DNA and enzymes were used as indicated in panel A. Hybridization was performed with the same probe as in A, but in non-stringent conditions. As described in Example 1 washing was for one hour in 2×SSC, 0.1% SDS at 40° C. (panel 1) and after exposure, the same filter was re-washed in 0.1× SSC, 0.1% SDS at 60° C. (panel 2). The autoradiographs were obtained after overnight exposition with intensifying screens.

From an initial survey of the restriction maps for certain of the HIV-2 isolates obtained according to the methods described herein, it is already apparent that HIV-2, like HIV-1, undergoes restriction site polymorphism. FIG. 4 A depicts examples of such differences for three isolates, all different one from another and from the cloned HIV-2$_{ROD}$. It is very likely that these differences at the nucleotide level are accompanied by variations in the amino-acid sequence of the viral proteins, as evidenced in the case of HIV-1 and described by M. Alizon et al. in Cell 46: 63–74 (1986), specifically incorporated herein by reference. It is also to be expected that the various isolates of HIV-2 will exhibit amino acid heterogeneities. See, for example, Clavel et al., *Nature* 324 (18):691–695 (1986), specifically incorporated herein by reference.

Further, the characterization of HIV-2 will also delineate the domain of the envelope glycoprotein that is responsible for the binding of the surface of the target cells and the subsequent internalization of the virus. This interaction was shown to be mediated by the CD4 molecule itself in the case of HIV-1 and similar studies tend to indicate that HIV-2 uses the same receptor. Thus, although there is wide divergence between the env genes of HIV-1 and 2, small homologous domains of the envelopes of the two HIV could represent a candidate receptor binding site. This site could be used to raise a protective immune response against this group of retroviruses.

From the data discussed herein, certain nucleotide sequences have been identified which are capable of being used as probes in diagnostic methods to obtain the immunological reagents necessary to diagnose an HIV-2 infection. In particular, these sequences may be used as probes in hybridization reactions with the genetic material of infected patients to indicate whether the RNA of the HIV-2 virus is present in these patient's lymphocytes or whether an analogous DNA is present. In this embodiment, the test methods which may be utilized include Northern blots, Southern blots and dot blots. One particular nucleotide sequence which may be useful as a probe is the combination of the 5 kb. HindIII fragment of ROD 4 and the E2 cDNA used in FIG. 4.

In addition, the genetic sequences of the HIV-2 virus may be used to create the polypeptides encoded by these sequences. Specifically, these polypeptides may be created by expression of the cDNA obtained according to the teachings herein in hosts such as bacteria, yeast or animal cells. These polypeptides may be used in diagnostic tests such as immunofluorescence assays (IFA), radioimmunoassays. (RIA) and Western Blot tests.

Moreover, it is also contemplated that additional diagnostic tests, including additional immunodiagnostic tests, may be developed in which the DNA probes or the polypeptides of this invention may serve as one of the diagnostic reagents. The invention described herein includes these additional test methods.

In addition, monoclonal antibodies to these polypeptides or fragments thereof may be created. The monoclonal antibodies may be used in immunodiagnostic tests in an analogous manner as the polypeptides described above.

The polypeptides of the present invention may also be used as immunogenic reagents to induce protection against infection by HIV-2 viruses. In this embodiment, the polypeptides produced by recombinant-DNA techniques would function as vaccine agents.

Also, the polypeptides of this invention may be used in competitive assays to test the ability of various antiviral agents to determine their ability to prevent the virus from fixing on its target.

Thus, it is to be understood that application of the teachings of the present invention to a specific problem or environment will be within the capabilities of one having ordinary skill in the art in light of the teachings contained herein. Examples of the products of the present invention and representative processes for their isolation and manufacture appear above and in the following examples.

EXAMPLES

Example 1

Cloning of a cDNA Complementary to Genomic RNA From HIV-2 Virions

HIV-2 virions were purified from 5 liters of supernatant from a culture of the CEM cell line infected with the ROD isolate and a cDNA first strand using oligo (dT) primer was synthesized in detergent activated endogenous reaction on pelleted virus, as described by M. Alizon et al. in Nature, 312: 757–760 (1984), specifically incorporated herein by reference. RNA-cDNA hybrids were purified by phenolchloroform extraction and ethanol precipitation. The second-strand cDNA was created by the DNA polymerase I/RNAase H method of Gubler and Hoffman in Gene, 25: 263–269 (1983), specifically incorporated herein by reference, using a commercial cDNA synthesis kit obtained from Amersham. After attachment of EcoRI linkers (obtained from Pharmacia), EcoRI digestion, and ligation into EcoRI-digested dephosphorylated M13 tg 130 vector (obtained from Amersham), a cDNA library was obtained by transformation of the *E. coli* TG1 strain. Recombinant plaques (104) were screened in situ on replica filters with the 1.5 kb. HindIII fragment from clone J19, corresponding to the 3' part of the genome of the LAVBRU isolate of HIV-1, $^{32}$p labelled to a specific activity of $10^9$cpm ug. The filters were prehybridized in 5×SSC, 5×Denhardt solution, 25% formamide, and denatured salmon sperm DNA (100 ug/ml.) at 37° C. for 4 hours and hybridized for 16 hours in the same buffer (Tm −42° C.) plus $4\times10^7$ cpm of the labelled probe ($10^6$ cpm/ml. of hybridization buffer). The washing was done in 5×SSC, 0.1% SDS at 25° C. for 2 hours. 20×SSC is 3 M NaCl, 0.3 M Na citrate. Positive plaques were purified and single-stranded M13 DNA prepared and end-sequenced according to the method described in Proc. Nat'l. Acad. Sci. USA, 74: 5463–5467 (1977) of Sanger et al.

Example 2

Hybridization of DNA from HIV-1 and HIV-2 Infected Cells and RNA from HIV-1 and 2 and SIV Virons With a Probe Derived From an HIV-2 Cloned cDNA DNA was extracted from infected CEM cells continuously producing HIV-1 or 2. The DNA digested with 20 ug of PstI digested with or undigested, was electrophoresed on a 0.8% agarose gel, and Southern-transferred to nylon membrane. Virion dot-blots were prepared in duplicate, as described by F. Clavel et al. in Science 233: 343–346 (1986), specifically incorporated herein by reference, by pelleting volumes of supernatant corresponding to the same amount of reverse transcriptase activity. Prehybridization was done in 50% formamide, 5×SSC, 5×Denhardt solution, and 100 mg./ml. denatured salmon sperm DNA for 4 hours at 42° C. Hybridization was performed in the same buffer plus 10% Dextran sulphate, and $10^6$ cpm/ml. of the labelled E2 insert (specific activity $10^9$ cpm/ug.) for 16 hours at 42° C. Washing was in 0.1×SSC, 0.1% SDS for 2 ×30 mn. After exposition for 16 hours with intensifying screens, the Southern blot was dehybridized in 0.4 N NaOH, neutralized, and rehybridized in the same conditions to the HIV-1 probe labelled to $10^9$ cpm/ug.

Example 3

Cloning in Lambda Phage of the Complete Provirus DNA of HIV-2

DNA from the HIV-2$^{ROD}$ infected CEM (FIG. 2, lanes a and c) was partially digested with Sau3AI. The 9–15 kb. fraction was selected on a 5–40% sucrose gradient and ligated to BamHI arms of the lambda L47.1 vector. Plaques (2×106) obtained after in vitro packaging and plating on *E. coli* LA 101 strain were screened in situ with the insert from the E2 cDNA clone. Approximately 10 positive clones were plaque purified and propagated on *E. coli* C600 recBC. The ROD 4, 27, and 35 clones were amplified and their DNA characterized by restriction mapping and Southern blotting with the HIV-2 cDNA clone under stringent conditions, and gag-pol probes from HIV-1 used under non stringent conditions.

Example 4

Complete Genomic Sequence of the ROD HIV-2 Isolate

Experimental analysis of the HIV-2 ROD isolate yielded the following sequence which represents the complete genome of this HIV-2 isolate. Genes and major expression products identified within the following sequence are indicated by nucleotides numbered below:

1) GAG gene (546–2111) expresses a protein product having a molecular weight of around 55Kd and is cleaved into the following proteins:
   a) p 16 (546–950)
   b) p 26 (951–1640)
   c) p 12 (1701–2111)
2) polymerase (1829–4936)
3) Q protein (4869–5513)
4) R protein (5682–5996)
5) X protein (5344–5679)
6) Y protein (5682–5996)
7) Env protein (6147–8720)
8) F protein (8557–9324) 9) TAT gene (5845–6140 and 8307–8400) is expressed by two exons separated by introns.
10) ART protein (6071–6140 and 8307–8536) is similarly the expression product of two exons.
11) LTR:R (1–173 and 9498–9671)
12) U5 (174–299)
13) U3 (8942–9497)

It will be known to one of skill in the art that the absolute numbering which has been adopted is not essential. For example, the nucleotide within the LTR which is designated as "1" is a somewhat arbitrary choice. What is important is the sequence information provided.

```
GGTCGCTCTGCGGAGAGGCTGGCAGATTGAGCCCTGGGAGGTTCTCTCCAGCACTAGCAG
     *         *         *         *         *         *

GTAGAGCCTGGGTGTTCCCTGCTAGACTCTCACCAGCACTTGGCCGGTGCTGGGCAGACG
     *         *         *        100        *         *

GCCCCACGCTTGCTTGCTTAAAAACCTCTTAATAAAGCTGCCAGTTAGAAGCAAGTTAAG
     *         *         *         *         *         *

TGTGTGCTCCCATCTCTCCTAGTCGCCGCCTGGTCATTCGGTGTTCACCTGAGTAACAAG
     *        200        *         *         *         *

ACCCTGGTCTGTTAGGACCCTTCTTGCTTTGGGAAACCGAGGCAGGAAAATCCCTAGCAG
     *         *         *         *         *        300

GTTGGCGCCTGAACAGGGACTTGAAGAAGACTGAGAAGTCTTGGAACACGGCTGAGTGAA
```

-continued

```
GGCAGTAAGGGCGGCAGGAACAAACCACGACGGAGTGCTCCTAGAAAGGCGCGGGCCGAG
         *         *         *        400        *         *
GTACCAAAGGCAGCGTGTGGAGCGGGAGGAGAAGAGGCCTCCGGGTGAAGGTAAGTACCT
         *         *         *         *         *         *
ACACCAAAAACTGTAGCCGAAAGGGCTTGCTATCCTACCTTTAGACAGGTAGAAGATTGT
         *        500        *         *         *         *
```

MetGlyAlaArgAsnSerValLeuArgGlyLysLysAlaAspGluLeuGluArgIle
```
GGGAGATGGGCGCGAGAAACTCCGTCTTGAGAGGGAAAAAAGCAGATGAATTAGAAAGAA
         *         *         *         *         *        600
```

ArgLeuArgProGlyGlyLysLysLysTyrArgLeuLysHisIleValTrpAlaAlaAsn
```
TCAGGTTACGGCCCGGCGGAAAGAAAAAGTACAGGCTAAAACATATTGTGTGGGCAGCGA
         *         *         *         *         *         *
```

LysLeuAspArgPheGlyLeuAlaGluSerLeuLeuGluSerLysGluGlyCysGlnLys
```
ATAAATTGGACAGATTCGGATTAGCAGAGAGCCTGTTGGAGTCAAAAGAGGGTTGTCAAA
         *         *         *        700        *         *
```

IleLeuThrValLeuAspProMetValProThrGlySerGluAsnLeuLysSerLeuPhe
```
AAATTCTTACAGTTTTAGATCCAATGGTACCGACAGGTTCAGAAAATTTAAAAAGTCTTT
         *         *         *         *         *         *
```

AsnThrValCysValIleTrpCysIleHisAlaGluGluLysValLysAspThrGluGly
```
TTAATACTGTCTGCGTCATTTGGTGCATACACGCAGAAGAGAAAGTGAAAGATACTGAAG
         *        800        *         *         *         *
```

AlaLysGlnIleValArgArgHisLeuValAlaGluThrGlyThrAlaGluLysMetPro
```
GAGCAAAACAAATAGTGCGGAGACATCTAGTGGCAGAAACAGGAACTGCAGAGAAAATGC
         *         *         *         *         *        900
```

SerThrSerArgProThrAlaProSerSerGluLysGlyGlyAsnTyrProValGlnHis
```
CAAGCACAAGTAGACCAACAGCACCATCTAGCGAGAAGGGAGGAAATTACCCAGTGCAAC
         *         *         *         *         *         *
```

ValGlyGlyAsnTyrThrHisIleProLeuSerProArgThrLeuAsnAlaTrpValLys
```
ATGTAGGCGGCAACTACACCCATATACCGCTGAGTCCCCGAACCCTAAATGCCTGGGTAA
         *         *         *       1000        *         *
```

LeuValGluGluLysLysPheGlyAlaGluValValProGlyPheGlnAlaLeuSerGlu
```
AATTAGTAGAGGAAAAAAGTTCGGGGCAGAAGTAGTGCCAGGATTTCAGGCACTCTCAG
         *         *         *         *         *         *
```

GlyCysThrProTyrAspIleAsnGlnMetLeuAsnCysValGlyAspHisGlnAlaAla
```
AAGGCTGCACGCCCTATGATATCAACCAAATGCTTAATTGTGTGGGCGACCATCAAGCAG
         *       1100        *         *         *         *
```

MetGlnIleIleArgGluIleIleAsnGluGluAlaAlaGluTrpAspValGlnLisPro
```
CCATGCAGATAATCAGGGAGATTATCAATGAGGAAGCAGCAGAATGGGATGTGCAACATC
         *         *         *         *         *       1200
```

IleProGlyProLeuProAlaGlyGlnLeuArgGluProArgGlySerAspIleAlaGly
```
CAATACCAGGCCCCTTACCAGCGGGGCAGCTTAGAGAGCCAAGGGGATCTGACATAGCAG
         *         *         *         *         *         *
```

ThrThrSerThrValGluGluGlnIleGlnTrpMetPheArgProGlnAsnProValPro
```
GGACAACAAGCACAGTAGAAGAACAGATCCAGTGGATGTTTAGGCCACAAAATCCTGTAC
         *         *         *       1300        *         *
```

ValGlyAsnIleTyrArgArgTrpIleGlnIleGlyLeuGlnLysCysValArgMetTyr
```
CAGTAGGAAACATCTATAGAAGATGGATCCAGATAGGATTGCAGAAGTGTGTCAGGATGT
         *         *         *         *         *         *
```

AsnProThrAsnIleLeuAspIleLysGlnGlyProLysGluProPheGlnSerTyrVal
```
ACAACCCGACCAACATCCTAGACATAAAACAGGGACCAAAGGAGCCGTTCCAAAGCTATG
         *       1400        *         *         *         *
```

AspArgPheTyrLysSerLeuArgAlaGluGlnThrAspProAlaValLysAsnTrpMet
```
TAGATAGATTCTACAAAAGCTTGAGGGCAGAACAAACAGATCCAGCAGTGAAGAATTGGA
         *         *         *         *         *       1500
```

ThrGlnThrLeuLeuValGlnAsnAlaAsnProAspCysLysLeuValLeuLysGlyLeu
```
TGACCCAAACACTGCTAGTACAAAATGCCAACCCAGACTGTAAATTAGTGCTAAAAGGAC
         *         *         *         *         *         *
```

GlyMetAsnProThrLeuGluGluMetLeuThrAlaCysGlnGlyValGlyGlyProGly

-continued

```
TAGGGATGAACCCTACCTTAGAAGAGATGCTGACCGCCTGTCAGGGGGTAGGTGGGCCAG
      *         *         *        1600        *         *

GlnLysAlaArgLeuMetAlaGluAlaLeuLysGluValIleGlyProAlaProIlePro
GCCAGAAAGCTAGATTAATGGCAGAGGCCCTGAAAGAGGTCATAGGACCTGCCCCTATCC
      *         *         *         *         *         *

PheAlaAlaAlaGlnGlnArgLysAlaPheLysCysTrpAsnCysGlyLysGluGlyHis
CATTCGCAGCAGCCCAGCAGAGAAAGGCATTTAAATGCTGGAACTGTGGAAAGGAAGGGC
      *        1700        *         *         *         *

SerAlaArgGlnCysArgAlaProArgArgGlnGlyCysTrpLysCysGlyLysProGly
ACTCGGCAAGACAATGCCGAGCACCTAGAAGGCAGGGCTGCTGGAAGTGTGGTAAGCCAG
      *         *         *         *         *        1800

ThrGlyArgPhePheArgThrGlyProLeuGly
   HisIleMetThrAsnCysProAspArgGlnAlaGlyPheLeuGlyLeuGlyProTrpGly
GACACATCATGACAAACTGCCCAGATAGACAGGCAGGTTTTTTAGGACTGGGCCCTTGGG
      *         *         *         *         *         *

LysGluAlaProGlnLeuProArgGlyProSerSerAlaGlyAlaAspThrAsnSerThr
   LysLysProArgAsnPheProValAlaGlnValProGlnGlyLeuThrProThrAlaPro
GAAAGAAGCCCCGCAACTTCCCCGTGGCCCAAGTTCCGCAGGGGCTGACACCAACAGCAC
      *         *         *        1900        *         *

ProSerGlySerSerSerGlySerThrGlyGluIleTyrAlaAlaArgGluLysThrGlu
     ProValAspProAlaValAspLeuLeuGluLysTyrMetGlnGlnGlyLysArgGlnArg
CCCCAGTGGATCCAGCAGTGGATCTACTGGAGAAATATATGCAGCAAGGGAAAAGACAGA
      *         *         *         *         *         *

ArgAlaGluArgGluThrIleGlnGlySerAspArgGlyLeuThrAlaProArgAlaGly
     GluGlnArgGluArgProTyrLysGluValThrGluAspLeuLeuHisLeuGluGlnGly
GAGAGCAGAGAGAGACCATACAAGGAAGTGACAGAGGACTTACTGCACCTCGAGCAGG
      *         *        2000        *         *         *

GlyAspThrIleGlnGlyAlaThrAsnArgGlyLeuAlaAlaProGlnPheSerLeuTrp
     GluThrProTyrArgGluProProThrGluAspLeuLeuHisLeuAsnSerLeuPheGly
GGGAGACACCATACAGGGAGCCACCAACAGAGGACTTGCTGCACCTCAATTCTCTCTTTG
      *         *         *         *         *        2100

LysArgProValValThrAlaTyrIleGluGlyGlnProValGluValLeuLeuAspThr
   LysAspGln
GAAAAGACCAGTAGTCACAGCATACATTGAGGGTCAGCCAGTAGAAGTCTTGTTAGACAC
      *         *         *         *         *         *

GlyAlaAspAspSerIleValAlaGlyIleGluLeuGlyAsnAsnTyrSerProLysIle
AGGGGCTGACGACTCAATAGTAGCAGGAATAGAGTTAGGGAACAATTATAGCCCAAAAAT
      *         *         *        2200        *         *

ValGlyGlyIleGlyGlyPheIleAsnThrLysGluTyrLysAsnValGluIleGluVal
AGTAGGGGGAATAGGGGGATTCATAAATACCAAGGAATATAAAAATGTAGAAATAGAAGT
      *         *         *         *         *         *

LeuAsnLysLysValArgAlaThrIleMetThrGlyAspThrProIleAsnIlePheGly
TCTAAATAAAAAGGTACGGGCCACCATAATGACAGGCGACACCCCAATCAACATTTTTGG
      *         *         *        2300        *         *

ArgAsnIleLeuThrAlaLeuGlyMetSerLeuAsnLeuProValAlaLysValGluPro
CAGAAATATTCTGACAGCCTTAGGCATGTCATTAAATCTACCAGTCGCCAAAGTAGAGCC
      *         *         *         *         *        2400

IleLysIleMetLeuLysProGlyLysAspGlyProLysLeuArgGlnTrpProLeuThr
AATAAAAATAATGCTAAAGCCAGGGAAAGATGGACCAAAACTGAGACAATGGCCCTTAAC
      *         *         *         *         *         *

LysGluLysIleGluAlaLeuLysGluIleCysGluLysMetGluLysGluGlyGlnLeu
AAAAGAAAAAATAGAAGCACTAAAAGAAATCTGTGAAAAAATGGAAAAAGAAGGCCAGCT
      *         *         *        2500        *         *

GluGluAlaProProThrAsnProTyrAsnThrProThrPheAlaIleLysLysLysAsp
AGAGGAAGCACCTCCAACTAATCCTTATAATACCCCCACATTTGCAATCAAGAAAAAGGA
      *         *         *         *         *         *

LysAsnLysTrpArgMetLeuIleAspPheArgGluLeuAsnLysValThrGlnAspPhe
CAAAAACAAATGGAGGATGCTAATAGATTTCAGAGAACTAAACAAGGTAACTCAAGATTT
      *        2600        *         *         *         *

ThrGluIleGlnLeuGlyIleProHisProAlaGlyLeuAlaLysLysArgArgIleThr
CACAGAAATTCAGTTAGGAATTCCACACCCAGCAGGGTTGGCCAAGAAGAGAAGAATTAC
      *         *         *         *         *        2700
```

-continued

```
ValLeuAspValGlyAspAlaTyrPheSerIleProLeuHisGluAspPheArgProTyr
TGTACTAGATGTAGGGGATGCTTACTTTTCCATACCACTACATGAGGACTTTAGACCATA
      *         *         *         *         *         *

ThrAlaPheThrLeuProSerValAsnAsnAlaGluProGlyLysArgTyrIleTyrLys
TACTGCATTTACTCTACCATCAGTGAACAATGCAGAACCAGGAAAAAGATACATATATAA
      *         *         *        2800         *         *

ValLeuProGlnGlyTrpLysGlySerProAlaIlePheGlnHisThrMetArgGlnVal
AGTCTTGCCACAGGGATGGAAGGGATCACCAGCAATTTTTCAACACACAATGAGACAGGT
      *         *         *         *         *         *

LeuGluProPheArgLysAlaAsnLysAspValIleIleIleGlnTyrMetAspAspIle
ATTAGAACCATTCAGAAAAGCAAACAAGGATGTCATTATCATTCAGTACATGGATGATAT
      *        2900         *         *         *         *

LeuIleAlaSerAspArgThrAspLeuGluHisAspArgValValLeuGlnLeuLysGlu
CTTAATAGCTAGTGACAGGACAGATTTAGAACATGATAGGGTAGTCCTGCAGCTCAAGGA
      *         *         *         *         *        3000

LeuLeuAsnGlyLeuGlyPheSerThrProAspGluLysPheGlnLysAspProProTyr
ACTTCTAAATGGCCTAGGATTTTCTACCCCAGATGAGAAGTTCCAAAAAGACCCTCCATA
      *         *         *         *         *         *

HisTrpMetGlyTyrGluLeuTrpProThrLysTrpLysLeuGlnLysIleGlnLeuPro
CCACTGGATGGGCTATGAACTATGGCCAACTAAATGGAAGTTGCAGAAAATACAGTTGCC
      *         *         *        3100         *         *

GlnLysGluIleTrpThrValAsnAspIleGlnLysLeuValGlyValLeuAsnTrpAla
CCAAAAAGAAATATGGACAGTCAATGACATCCAGAAGCTAGTGGGTGTCCTAAATTGGGC
      *         *         *         *         *         *

AlaGlnLeuTyrProGlyIleLysThrLysHisLeuCysArgLeuIleArgGlyLysMet
AGCACAACTCTACCCAGGGATAAAGACCAAACACTTATGTAGGTTAATCAGAGGAAAAAT
      *         *        3200         *         *         *

ThrLeuThrGluGluValGlnTrpThrGluLeuAlaGluAlaGluLeuGluGluAsnArg
GACAGTCACAGAAGAAGTACAGTGGACAGAATTAGCAGAAGCAGAGCTAGAAGAAAACAG
      *         *         *         *         *        3300

IleIleLeuSerGlnGluGlnGluGlyHisTyrTyrGlnGluGluLysGluLeuGluAla
AATTATCCTAAGCCAGGAACAAGAGGGACACTATTACCAAGAAGAAAAAGAGCTAGAAGC
      *         *         *         *         *         *

ThrValGlnLysAspGlnGluAsnGlnTrpThrTyrLysIleHisGlnGluGluLysIle
AACAGTCCAAAAGGATCAAGAGAATCAGTGGACATATAAAATACACCAGGAAGAAAAAAT
      *         *         *        3400         *         *

LeuLysValGlyLysTyrAlaLysValLysAsnThrHisThrAsnGlyIleArgLeuLeu
TCTAAAAGTAGGAAAATATGCAAAGGTGAAAAACACCCATACCAATGGAATCAGATTGTT
      *         *         *         *         *         *

AlaGlnValValGlnLysIleGlyLysGluAlaLeuValIleTrpGlyArgIleProLys
AGCACAGGTAGTTCAGAAAATAGGAAAAGAAGCACTAGTCATTTGGGGACGAATACCAAA
      *         *        3500         *         *         *

PheHisLeuProValGluArgGluIleTrpGluGlnTrpTrpAspAsnTyrTrpGlnVal
ATTTCACCTACCAGTAGAGAGAGAAATCTGGGAGCAGTGGTGGGATAACTACTGGCAAGT
      *         *         *         *         *        3600

ThrTrpIleProAspTrpAspPheValSerThrProProLeuValArgLeuAlaPheAsn
GACATGGATCCCAGACTGGGACTTCGTGTCTACCCCACCACTGGTCAGGTTAGCGTTTAA
      *         *         *         *         *         *

LeuValGlyAspProIleProGlyAlaGluThrPheTyrThrAspGlySerCysAsnArg
CCTGGTAGGGGATCCTATACCAGGTGCAGAGACCTTCTACACAGATGGATCCTGCAATAG
      *         *         *         *        3700         *

GlnSerLysGluGlyLysAlaGlyTyrValThrAspArgGlyLysAspLysValLysLys
GCAATCAAAAGAAGGAAAAGCAGGATATGTAACAGATAGGGGAAAGACAAGGTAAAGAA
      *         *         *         *         *         *

LeuGluGlnThrThrAsnGlnGlnAlaGluLeuGluAlaPheAlaMetAlaLeuThrAsp
ACTAGAGCAAACTACCAATCAGCAAGCAGAACTAGAAGCCTTTGCGATGGCACTAACAGA
      *        3800         *         *         *         *

SerGlyProLysValAsnIleIleValAspSerGlnTyrValMetGlyIleSerAlaSer
CTCGGGTCCAAAAGTTAATATTATAGTAGACTCACAGTATGTAATGGGGATCAGTGCAAG
      *         *         *         *         *        3900
```

```
                         -continued

GlnProThrGluSerGluSerLysIleValAsnGlnIleIleGluGluMetIleLysLys
    CCAACCAACAGAGTCAGAAAGTAAAATAGTCAACCAGATCATAGAAGAAATGATAAAAAA
         *         *         *         *         *         *

GluAlaIleTyrValAlaTrpValProAlaHisLysGlyIleGlyGlyAsnGlnGluVal
    GGAAGCAATCTATGTTGCATGGGTCCCAGCCCACAAAGGCATAGGGGGAAACCAGGAAGT
         *         *         *       4000         *         *

AspHisLeuValSerGlnGlyIleArgGlnValLeuPheLeuGluLysIleGluProAla
    AGATCATTTAGTGAGTCAGGGTATCAGACAAGTGTTGTTCCTGGAAAAAATAGAGCCCGC
         *         *         *         *         *         *

GlnGluGluHisGluLysTyrHisSerAsnValLysGluLeuSerHisLysPheGlyIle
    TCAGGAAGAACATGAAAAATATCATAGCAATGTAAAAGAACTGTCTCATAAATTTGGAAT
         *       4100         *         *         *         *

ProAsnLeuValAlaArgGlnIleValAsnSerCysAlaGlnCysGlnGlnLysGlyGlu
    ACCCAATTTAGTGGCAAGGCAAATAGTAAACTCATGTGCCCAATGTCAACAGAAAGGGGA
         *         *         *         *         *       4200

AlaIleHisGlyGlnValAsnAlaGluLeuGlyThrTrpGlnMetAspCysThrHisLeu
    AGCTATACATGGGCAAGTAAATGCAGAACTAGGCACTTGGCAAATGGACTGCACACATTT
         *         *         *         *         *         *

GluGlyLysIleIleIleValAlaValHisValAlaSerGlyPheIleGluAlaGluVal
    AGAAGGAAAGATCATTATAGTAGCAGTACATGTTGCAAGTGGATTTATAGAAGCAGAAGT
         *         *         *       4300         *         *

IleProGlnGluSerGlyArgGlnThrAlaLeuPheLeuLeuLysLeuAlaSerArgTrp
    CATCGCACAGGAATCAGGAAGACAAACAGCACTCTTCCTATTGAAACTGGCAAGTAGGTG
         *         *         *         *         *         *

ProIleThrHisLeuHisThrAspAsnGlyAlaAsnPheThrSerGlnGluValLysMet
    GCCAATAACACACTTGCATACAGATAATGGTGCCAACTTCACTTCACAGGAGGTGAAGAT
         *         *       4400         *         *         *

ValAlaTrpTrpIleGlyIleGluGlnSerPheGlyValProTyrAsnProGlnSerGln
    GGTAGCATGGTGGATAGGTATAGAACAATCCTTTGGAGTACCTTACAATCCACAGAGCCA
         *         *         *         *         *       4500

GlyValValGluAlaMetAsnHisHisLeuLysAsnGluIleSerArgIleArgGluGln
    AGGAGTAGTAGAAGCAATGAATCACCATCTAAAAAACCAAATAAGTAGAATCAGAGAACA
         *         *         *         *         *         *

AlaAsnThrIleGluThrIleValLeuMetAlaIleHisCysMetAsnPheLysArgArg
    GGCAAATACAATAGAAACAATAGTACTAATGGCAATTCATTGCATGAATTTTAAAAGAAG
         *         *         *         *       4600         *

GlyGlyIleGlyAspMetThrProSerGluArgLeuIleAsnMetIleThrThrGluGln
    GGGGGGAATAGGGGATATGACTCCATCAGAAAGATTAATCAATATGATCACCACAGAACA
         *         *         *         *         *         *

GluIleGlnPheLeuGlnAlaLysAsnSerLysLeuLysAspPheArgValTyrPheArg
    AGAGATACAATTCCTCCAAGCCAAAAATTCAAAATTAAAAGATTTTCGGGTCTATTTCAG
         *       4700         *         *         *         *

GluGlyArgAspGluLeuTrpLysGlyProGlyGluLeuLeuTrpLysGlyGluGlyAla
    AGAAGGCAGAGATCAGTTGTGGAAAGGACCTGGGGAACTACTGTGGAAAGGAGAAGGAGC
         *         *         *         *         *       4800

ValLeuValLysValGlyThrAspIleLysIleIleProArgArgLysAlaLysIleIle
    AGTCCTAGTCAAGGTAGGAACAGACATAAAAATAATACCAAGAAGGAAAGCCAAGATCAT
         *         *         *         *         *         *

ArgAspTyrGlyGlyArgGlnGluMetAspSerGlySerHisLeuGluGlyAlaArgGlu
            MetGluGluAspLysArgTrpIleValValProThrTrpArgValProGlyArg
    CAGAGACTATGGAGGAAGACAAGAGATGGATAGTGGTTCCCACCTGGAGGGTGCCAGGGA
         *         *         *       4900         *         *

AspGlyGluMetAla
     MetGluLysTrpHisSerLeuValLysTyrLeuLysTyrLysThrLysAspLeuGluLys
    GGATGGAGAAATGGCATAGCCTTGTCAAGTATCTAAAATACAAAACAAAGGATCTAGAAA
         *         *         *         *         *         *

ValCysTyrValProHisHisLysValGlyTrpAlaTrpTrpThrCysSerArgValIle
    AGGTGTGCTATGTTCCCCACCATAAGGTGGGATGGGCATGGTGGACTTGCAGCAGGGTAA
             *       5000         *         *         *         *

PheProLeuLysGlyAsnSerHisLeuGluIleGlnAlaTyrTrpAsnLeuThrProGlu
```

-continued

```

TATTCCCATTAAAAGGAAACAGTCATCTAGAGATACAGGCATATTGGAACTTAACACCAG
         *         *         *         *         *      5100

LysGlyTrpLeuSerSerTyrSerValArgIleThrTrpTyrThrGluLysPheTrpThr
AAAAAGGATGGCTCTCCTCTTATTCAGTAAGAATAACTTGGTACACAGAAAAGTTCTGGA
         *         *         *         *         *         *

AspValThrProAspCysAlaAspValLeuIleHisSerThrTyrPheProCysPheThr
CAGATGTTACCCCAGACTGTGCAGATGTCCTAATACATAGCACTTATTTCCCTTGCTTTA
         *         *         *      5200          *         *

AlaGlyGluValArgArgAlaIleArgGlyGluLysLeuLeuSerCysCysAsnTyrPro
CAGCAGGTGAAGTAAGAAGAGCCATCAGAGGGGAAAAGTTATTGTCCTGCTGCAATTATC
         *         *         *         *         *         *

ArgAlaHisArgAlaGlnValProSerLeuGlnPheLeuAlaLeuValValValGlnGln
CCCGAGCTCATAGAGCCCAGGTACCGTCACTTCAATTTCTGGCCTTAGTGGTAGTGCAAC
         *      5300          *         *         *         *

MetThrAspProArgGluThrValProProGlyAsnSerGlyGluGluThrIleGly
     AsnAspArgProGlnArgAspSerThrThrArgLysGlnArgArgArgAspTyrArgArg
AAAATGACAGACCCCAGAGAGACAGTACCACCAGGAAACAGCGGCGAAGAGACTATCGGA
         *         *         *         *         *      5400

GluAlaPheAlaTrpLeuAsnArgThrValGluAlaIleAsnArgGluAlaValAsnHis
    GlyLeuArgLeuAlaLysGlnAspSerArgSerHisLysGlnArgSerSerGluSerPro
GAGGCCTTCGCCTGGCTAAACAGGACAGTAGAAGCCATAAACAGAGAAGCAGTGAATCAC
         *         *         *         *         *         *

LeuProArgGluLeuIlePheGlnValTrpGlnArgSerTrpArgTyrTrpHisAspGlu
    ThrProArgThrTyrPheProGlyValAlaGluValLeuGluIleLeuAla
CTACCCCGAGAACTTATTTTCCAGGTGTGGCAGAGGTCCTGGAGATACTGGCATGATGAA
         *         *         *      5500          *         *

GlnGlyMetSerGluSerTyrThrLysTyrArgTyrLeuCysIleIleGlnLysAlaVal
CAAGGGATGTCAGAAAGTTACACAAAGTATAGATATTTGTGCATAATACAGAAAGCAGTG
         *         *         *         *         *         *

TyrMetHisValArgLysGlyCysThrCysLeuGlyArgGlyHisGlyProGlyGlyTrp
TACATGCATGTTAGGAAAGGGTGTACTTGCCTGGGGAGGGGACATGGGCCAGGAGGGTGG
         *      5600          *         *         *         *

ArgProGlyProProProProProProProGlyLeuVal
                                        MetAlaGluAlaProThrGlu
AGACCAGGGCCTCCTCCTCCTCCCCCTCCAGGTCTGGTCTAATGGCTGAAGCACCAACAG
         *         *         *         *         *      5700

LeuProProValAspGlyThrProLeuArgGluProGlyAspGluTrpIleIleGluIle
AGCTCCCCCCGGTGGATGGGACCCCACTGAGGGAGCCAGGGGATGAGTGGATAATAGAAA
         *         *         *         *         *         *

LeuArgGluIleLysGluGluAlaLeuLysHisPheAspProArgLeuLeuIleAlaLeu
TCTTGAGAGAAATAAAAGAAGAAGCTTTAAAGCATTTTGACCCTCGCTTGCTAATTGCTC
         *         *         *      5800          *         *

MetGluThrPreLeuLysAlaProGluSerSerLeu
     GlyLysTyrIleTyrThrArgHisGlyAspThrLeuGluGlyAlaArgGluLeuIleLys
TTGGCAAATATATCTATACTAGACATGGAGACACCCTTGAAGGCGCCAGAGAGCTCATTA
         *         *         *         *         *         *

LysSerCysAsnGluProPheSerArgThrSerGluGlnAspValAlaThrGlnGluLeu
    ValLeuGlnArgAlaLeuPheThrHisPheArgAlaGlyCysGlyHisSerArgIleGly
AAGTCCTGCAACGAGCCCTTTTCACGCACTTCAGAGCAGGATGTGGCCACTCAAGAATTG
         *      5900          *         *         *         *

AlaArgGlnGlyGluGluIleLeuSerGlnLeuTyrArgProLeuGluThrCysAsnAsn
    GlnThrArgGlyGlyAsnProLeuSerAlaIleProThrProArgAsnMetGln
GCCAGACAAGGGGAGGAAATCCTCTCTCAGCTATACCGACCCCTAGAAACATGCAATAAC
         *         *         *         *         *      6000

SerCysTyrCysLysArgCysCysTyrHisCysGlnMetCysPheLeuAsnLysGlyLeu
TCATGCTATTGTAAGCGATGCTGCTACCATTGTCAGATGTGTTTTCTAAACAAGGGGCTC
         *         *         *         *         *         *

GlyIleCysTyrGluArgLysGlyArgArgArgThrProLysLysThrLysThrHis
          MetAsnGluArgAlaAspGluGluGlyLeuGlnArgLysLeuArgLeuIle
GGGATATGTTATGAACGAAAGGGCAGACGAAGAAGGACTCCAAAGAAAACTAAGACTCAT
         *         *         *      6100          *         *

ProSerProThrProAspLys
```

```
                                                        -continued
ArgLeuLeuHisGlnThr
                              MetMetAsnGlnLeuLeuIleAlaIleLeuLeuAla
CCGTCTCCTACACCAGACAAGTGAGTATGATGAATCAGCTGCTTATTGCCATTTTATTAG
         *         *         *         *         *         *

SerAlaCysLeuValTyrCysThrGlnTyrValThrValPheTyrGlyValProThrTrp
CTAGTGCTTGCTTAGTATATTGCACCCAATATGTAACTGTTTTCTATGGCGTACCCACGT
         *       6200        *         *         *         *

LysAsnAlaThrIleProLeuPheCysAlaThrArgAsnArgAspThrTrpGlyThrIle
GGAAAAATGCAACCATTCCCCTCTTTTGTGCAACCAGAAATAGGGATACTTGGGGAACCA
         *         *         *         *         *       6300

GlnCysLeuProAspAsnAspAspTyrGlnGluIleThrLeuAsnValThrGluAlaPhe
TACAGTGCTTGCCTGACAATGATGATTATCAGGAAATAACTTTGAATGTAACAGAGGCTT
         *         *         *         *         *         *

AspAlaTrpAsnAsnThrValThrGluGlnAlaIleGluAspValTrpHisLeuPheGlu
TTGATGCATGGAATAATACAGTAACAGAACAAGCAATAGAAGATGTCTGGCATCTATTCG
         *         *         *       6400        *         *

ThrSerIleLysProCysValLysLeuThrProLeuCysValAlaMetLysCysSerSer
AGACATCAATAAAACCATGTGTCAAACTAACACCTTTATGTGTAGCAATGAAATGCAGCA
         *         *         *         *         *         *

ThrGluSerSerThrGlyAsnAsnThrThrSerLysSerThrSerThrThrThrThrThr
GCACAGAGAGCAGCACAGGGAACAACACAACCTCAAAGAGCACAAGCACAACCACAACCA
         *       6500        *         *         *         *

ProThrAspGlnGluGlnGluIleSerGluAspThrProCysAlaArgAlaAspAsnCys
CACCCACAGACCAGGAGCAAGAGATAAGTGAGGATACTCCATGCGCACGCGCAGACAACT
         *         *         *         *         *       6600

SerGlyLeuGlyGluGluGluThrIleAsnCysGlnPheAsnMetThrGlyLeuGluArg
GCTCAGGATTGGGAGAGGAAGAAACGATCAATTGCCAGTTCAATATGACAGGATTAGAAA
         *         *         *         *         *         *

AspLysLysLysGlnTyrAsnGluThrTrpTyrSerLysAspValValCysGluThrAsn
GAGATAAGAAAAAACAGTATAATGAAACATGGTACTCAAAAGATGTGGTTTGTGAGACAA
         *         *         *       6700        *         *

AsnSerThrAsnGlnThrGlnCysTyrMetAsnHisCysAsnThrSerValIleThrGlu
ATAATAGCACAAATCAGACCCAGTGTTACATGAACCATTGCAACACATCAGTCATCACAG
         *         *         *         *         *         *

SerCysAspLysHisTyrTrpAspAlaIleArgPheArgTyrCysAlaProProGlyTyr
AATCATGTGACAAGCACTATTGGGATGCTATAAGGTTTAGATACTGTGCACCACCGGGTT
         *       6800        *         *         *         *

AlaLeuLeuArgCysAsnAspThrAsnTyrSerGlyPheAlaProAsnCysSerLysVal
ATGCCCTATTAAGATGTAATGATACCAATTATTCAGGCTTTGCACCCAACTGTTCTAAAG
         *         *         *         *         *       6900

ValAlaSerThrCysThrArgMetMetGluThrGlnThrSerThrTrpPheGlyPheAsn
TAGTAGCTTCTACATGCACCAGGATGATGGAAACGCAAACTTCCACATGGTTTGGCTTTA
         *         *         *         *         *         *

GlyThrArgAlaGluAsnArgThrTyrIleTyrTrpHisGlyArgAspAsnArgThrIle
ATGGCACTAGAGCAGAGAATAGAACATATATCTATTGGCATGGCAGAGATAATAGAACTA
         *         *         *       7000        *         *

IleSerLeuAsnLysTyrTyrAsnLeuSerLeuHisCysLysArgProGlyAsnLysThr
TCATCAGCTTAAACAAATATTATAATCTCAGTTTGCATTGTAAGAGGCCAGGGAATAAGA
         *         *         *         *         *         *

ValLysGlnIleMetLeuMetSerGlyHisValPheHisSerHisTyrGlnProIleAsn
CAGTGAAACAAATAATGCTTATGTCAGGACATGTGTTTCACTCCCACTACCAGCCGATCA
         *       7100        *         *         *         *

LysArgProArgGlnAlaTrpCysTrpPheLysGlyLysTrpLysAspAlaMetGlnGlu
ATAAAAGACCCAGACAAGCATGGTGCTGGTTCAAAGGCAAATGGAAAGACGCCATGCAGG
         *         *         *         *         *       7200

ValLysGluThrLeuAlaLysHisProArgTyrArgGlyThrAsnAspThrArgAsnIle
AGGTGAAGGAAACCCTTGCAAAACATCCCAGGTATAGAGGAACCAATGACACAAGGAATA
         *         *         *         *         *         *

SerPheAlaAlaProGlyLysGlySerAspProGluValAlaTyrMetTrpThrAsnCys
TTAGCTTTGCAGCGCCAGGAAAAGGCTCAGACCCAGAAGTAGCATACATGTGGACTAACT
         *         *         *       7300        *         *
```

```
    ArgGlyGluPheLeuTyrCysAsnMetThrTrpPheLeuAsnTrpIleGluAsnLysThr
    GCAGAGGAGAGTTTCTCTACTGCAACATGACTTGGTTCCTCAATTGGATAGAGAATAAGA
          *         *         *         *         *         *

HisArgAsnTyrAlaProCysHisIleLysGlnIleIleAsnThrTrpHisLysValGly
    CACACCGCAATTATGCACCGTGCCATATAAAGCAAATAATTAACACATGGCATAAGGTAG
          *      7400         *         *         *         *

ArgAsnValTyrLeuProProArgGluGlyGluLeuSerCysAsnSerThrValThrSer
    GGAGAAATGTATATTTGCCTCCCAGGGAAGGGGAGCTGTCCTGCAACTCAACAGTAACCA
          *         *         *         *         *      7500

IleIleAlaAsnIleAspTrpGlnAsnAsnAsnGlnThrAsnIleThrPheSerAlaGlu
    GCATAATTGCTAACATTGACTGGCAAAACAATAATCAGACAAACATTACCTTTAGTGCAG
          *         *         *         *         *         *

ValAlaGluLeuTyrArgLeuGluLeuGlyAspTyrLysLeuValGluIleThrProIle
    AGGTGGCAGAACTATACAGATTGGAGTTGGGAGATTATAAATTGGTAGAAATAACACCAA
          *         *         *      7600         *         *

GlyPheAlaProThrLysGluLysArgTyrSerSerAlaHisGlyArgHisThrArgGly
    TTGGCTTCGCACCTACAAAAGAAAAAAGATACTCCTCTGCTCACGGGAGACATACAAGAG
          *         *         *         *         *         *

ValPheValLeuGlyPheLeuGlyPheLeuAlaThrAlaGlySerAlaMetGlyAlaAla
    GTGTGTTCGTGCTAGGGTTCTTGGGTTTTCTCGCAACAGCAGGTTCTGCAATGGGCGCGG
          *      7700         *         *         *         *

SerLeuThrValSerAlaGlnSerArgThrLeuLeuAlaGlyIleValGlnGlnGlnGln
    CGTCCCTGACCGTGTCGGCTCAGTCCCGGACTTTACTGGCCGGGATAGTGCAGCAACAGC
          *         *         *         *         *      7800

GlnLeuLeuAspValValLysArgGlnGlnGluLeuLeuArgLeuThrValTrpGlyThr
    AACAGCTGTTGGACGTGGTCAAGAGACAACAAGAACTGTTGCGACTGACCGTCTGGGGAA
          *         *         *         *         *         *

LysAsnLeuGlnAlaArgValThrAlaIleGluLysTyrLeuGlnAspGlnAlaArgLeu
    CGAAAAACCTCCAGGCAAGAGTCACTGCTATAGAGAAGTACCTACAGGACCAGGCGCGGC
          *         *         *      7900         *         *

AsnSerTrpGlyCysAlaPheArgGlnValCysHisThrThrValProTrpValAsnAsp
    TAAATTCATGGGGATGTGCGTTTAGACAAGTCTGCCACACTACTGTACCATGGGTTAATG
          *         *         *         *         *         *

SerLeuAlaProAspTrpAspAsnMetThrTrpGlnGluTrpGluLysGlnValArgTyr
    ATTCCTTAGCACCTGACTGGGACAATATGACGTGGCAGGAATGGGAAAAACAAGTCCGCT
          *      8000         *         *         *         *

LeuGluAlaAsnIleSerLysSerLeuGluGlnAlaGlnIleGlnGlnGluLysAsnMet
    ACCTGGAGGCAAATATCAGTAAAAGTTTAGAACAGGCACAAATTCAGCAAGAGAAAAATA
          *         *         *         *         *      8100

TyrGluLeuGlnLysLeuAsnSerTrpAspIlePheGlyAsnTrpPheAspLeuThrSer
    TGTATGAACTACAAAAATTAAATAGCTGGGATATTTTTGGCAATTGGTTTGACTTAACCT
          *         *         *         *         *         *

TrpValLysTyrIleGlnTyrGlyValLeuIleIleValAlaValIleAlaLeuArgIle
    CCTGGGTCAAGTATATTCAATATGGAGTGCTTATAATAGTAGCAGTAATAGCTTTAAGAA
          *         *         *      8200         *         *

ValIleTyrValValGlnMetLeuSerArgLeuArgLysGlyTyrArgProValPheSer
    TAGTGATATATGTAGTACAAATGTTAAGTAGGCTTAGAAAGGGCTATAGGCCTGTTTTCT
          *         *         *         *         *         *

SerIleSerThrArgThrGlyAspSerGlnPro
                                AsnProTyrProGlnGlyProGlyThrAlaSerGln
     SerProProGlyTyrIleGlnGlnIleHisIleHisLysAspArgGlyGlnProAlaAsn
    CTTCCCCCCCCGGTTATATCCAACAGATCCATATCCACAAGGACCGGGGACAGCCAGCCA
          *      8300         *         *         *         *

ThrLysLysGlnLysLysThrValGluAlaThrValGluThrAspThrGlyProGlyArg
      ArgArgAsnArgArgArgArgTrpLysGlnArgTrpArgGlnIleLeuAlaLeuAlaAsp
       GluGluThrGluGluAspGlyGlySerAsnGlyGlyAspArgTyrTrpProTrpProIle
    ACGAAGAAACAGAAGAAGACGGTGGAAGCAACAGGTGGAGACAGATACTGGCCCTGGCCGA
          *         *         *         *         *      8400

SerIleTyrThrPheProAspProProAlaAspSerProLeuAspGlnThrIleGlnHis
      AlaTyrIleHisPheLeuIleArgGlnLeuIleArgLeuLeuThrArgLeuTyrSerIle
    TAGCATATATACATTTCCTGATCCGCCAGCTGATTCGCCTCTTGACCAGACTATACAGCA
```

```
                                                           -continued
      *         *         *         *         *         *

LeuGlnGlyLeuThrIleGlnGluLeuProAspProProThrHisLeuProGluSerGln
    CysArgAspLeuLeuSerArgSerPheLeuThrLeuGlnLeuIleTyrGlnAsnLeuArg
  TCTGCAGGGACTTACTATCCAGGAGCTTCCTGACCCTCCAACTCATCTACCAGAATCTCA
      *         *         *        8500       *         *

ArgLeuAlaGluThr              MetGlyAlaSerGlySerLysLys
    AspTrpLeuArgLeuArgThrAlaPheLeuGlnTyrGlyCysGluTrpIleGlnGluAla
  GAGACTGGCTGAGACTTAGAACAGCCTTCTTGCAATATGGGTGCGAGTGGATCCAAGAAG
      *         *         *         *         *         *

HisSerArgProProArgGlyLeuGlnGluArgLeuLeuArgAlaArgAlaGlyAlaCys
    PheGlnAlaAlaAlaArgAlaThrArgGluThrLeuAlaGlyAlaCysArgGlyLeuTrp
  CATTCCAGGCCGCCGCGAGGGCTACAAGAGAGACTCTTGCGGGCGCGTGCAGGGGCTTGT
      *        8600       *         *         *         *

GlyGlyTyrTrpAsnGluSerGlyGlyGluTyrSerArgPheGlnGluGlySerAspArg
    ArgValLeuGluArgIleGlyArgGlyIleLeuAlaValProArgArgIleArgGlnGly
  GGAGGGTATTGGAACGAATCGGGAGGGGAATACTCGCGGTTCCAAGAAGGATCAGACAGG
      *         *         *         *         *        8700

GluGlnLysSerProSerCysGluGlyArgGlnTyrGlnGlnGlyAspPheMetAsnThr
    AlaGluIleAlaLeuLeu
  GAGCAGAAATCGCCCTCCTGTGAGGGACGGCAGTATCAGCAGGGAGACTTTATGAATACT
      *         *         *         *         *         *

ProTrpLysAspProAlaAlaGluArgGluLysAsnLeuTyrArgGlnGlnAsnMetAsp
  CCATGGAAGGACCCAGCAGCAGAAAGGGAGAAAAATTTGTACAGGCAACAAAATATGGAT
      *         *         *        8800       *         *

AspValAspSerAspAspAspAspGlnValArgValSerValThrProLysValProLeu
  GATGTAGATTCAGATGATGATGACCAAGTAAGAGTTTCTGTCACACCAAAAGTACCACTA
      *         *         *         *         *         *

ArgProMetThrHisArgLeuAlaIleAspMetSerHisLeuIleLysThrArgGlyGly
  AGACCAATGACACATAGATTGGCAATAGATATGTCACATTTAATAAAAACAAGGGGGGGA
      *        8900       *         *         *         *

LeuGluGlyMetPheTyrSerGluArgArgHisLysIleLeuAsnIleTyrLeuGluLys
  CTGGAAGGGATGTTTTACAGTGAAAGAAGACATAAAATCTTAAATATATACTTAGAAAAG
      *         *         *         *         *        9000

GluGluGlyIleIleAlaAspTrpGlnAsnTyrThrHisGlyProGlyValArgTyrPro
  GAAGAAGGGATAATTGCAGATTGGCAGAACTACACTCATGGGCCAGGAGTAAGATACCCA
      *         *         *         *         *         *

MetPhePheGlyTrpLeuTrpLysLeuValProValAspValProGlnGluGlyGluAsp
  ATGTTCTTTGGGTGGCTATGGAAGCTAGTACCAGTAGATGTCCCACAAGAAGGGGAGGAC
      *         *         *        9100       *         *

ThrGluThrHisCysLeuValHisProAlaGlnThrSerLysPheAspAspProHisGly
  ACTGAGACTCACTGCTTAGTACATCCAGCACAAACAAGCAAGTTTGATGACCCGCATGGG
      *         *         *         *         *         *

GluThrLeuValTrpGluPheAspProLeuLeuAlaTyrSerTyrGluAlaPheIleArg
  GAGACACTAGTCTGGGAGTTTGATCCCTTGCTGGCTTATAGTTACGAGGCTTTTATTCGG
      *        9200       *         *         *         *

TyrProGluGluPheGlyHisLysSerGlyLeuProGluGluGluTrpLysAlaArgLeu
  TACCCAGAGGAATTTGGGCACAAGTCAGGCCTGCCAGAGGAAGAGTGGAAGGCGAGACTG
      *         *         *         *         *        9300

LysAlaArgGlyIleProPheSer
  AAAGCAAGAGGAATACCATTTAGTTAAAGACAGGAACAGCTATACTTGGTCAGGGCAGGA
      *         *         *         *         *         *

AGTAACTAACAGAAACAGCTGAGACTGCAGGGACTTTCCAGAAGGGGCTGTAACCAAGGG
      *         *         *        9400       *         *

AGGGACATGGGAGGAGCTGGTGGGAACGCCCTCATATTCTCTGTATAAATATACCCGCT
      *         *         *         *         *         *

AGCTTGCATTGTACTTCGGTCGCTCTGCGGAGAGGCTGGCAGATTGAGCCCTGGGAGGTT
      *         *         *         *         *        9500

CTCTCCAGCAGTAGCAGGTAGAGCCTGGGTGTTCCCTGCTAGACTCTCACCAGCACTTGG
      *         *         *         *         *        9600
```

-continued
CCGGTGCTGGGCAGACGGCCCCACGCTTGCTTGCTTAAAAACCTCCTTAATAAAGCTGCC
   *          *          *          *          *          *

AGTTAGAAGCA
   *

Example 5

Sequences of the Coding Regions for the Envelope Protein and GAG Product of the ROD HIV-2 Isolate Through experimental analysis of the HIV-2 ROD isolate, the following sequences were identified for the regions encoding the env and gag gene products. One of ordinary skill in the art will recognize that the numbering for both gene regions which follow begins for convenience with "1" rather than the corresponding number for its initial nucleotide as given in Example 4, above, in the context of the complete genomic sequence.

```
MetMetAsnGluLeuLeuIleAlaIleLeuLeuAlaSerAlaCys
ATGATGAATCAGCTGCTTATTGCCATTTTATTAGCTAGTGCTTGC

*         *         *         *
LeuValTyrCysThrGlnTyrValThrValPheTyrGlyValPro
TTAGTATATTGCACCCAATATGTAACTGTTTTCTATGGCGTACCC

*         *         *         *         *
ThrTrpLysAsnAlaThrIleProLeuPheCysAlaThrArgAsa
ACGTGGAAAAATGCAACCATTCCCCTGTTTTGTGCAACCAGAAAT

100         *         *         *
ArgAspThrTrpGlyThrIleGlaCysLeuProAspAsaAspAsp
AGGGATACTTGGGGAACCATACAGTGCTTGCCTGACAATGATGAT

*         *         *         *         *
TyrGluGluIleThrLeuAsnValThrGluAlaPheAspAlaTrp
TATCAGGAAATAACTTTGAATGTAACAGAGGCTTTTGATGCATGG

*       200           *         *
AsnAsaThrValThrGluGlnAlaIleGluAspValTrpHisLeu
AATAATACAGTAACAGAACAAGCAATAGAAGATGTCTGGCATCTA

*         *         *         *         *
PheGluThrSerIleLysProCysValLysLeuThrProLeuCys
TTCGAGACATCAATAAAACCATGTGTGAAACTAACACCTTTATGT

*         *       300           *
ValAlaMetLysCysSerSerThrGluSerSerThrGlyAsnAsn
GTAGCAATGAAATGCAGCAGCACAGAGAGCAGCACAGGGAACAAC

*         *         *         *         *
ThrThrSerLysSerThrSerThrThrThrThrThrProThrAsp
ACAACCTCAAAGAGCACAAGCACAACCACAACCACACCCAGAGAC

*         *         *       400
GluGluGlnGluIleSerGluAspThrProCysAlaArgAlaAsp
CAGGAGCAAGAGATAAGTGAGGATACTCCATGCGCACGCGCACAC

*         *         *         *         *
AsnCysSerGlyLeuGlyGluGluGluThrIleAsnCysGlnPhe
AACTGCTCAGGATTGGGAGAGGAAGAAACGATCAATTGCCAGTTC

*         *         *         *
AsnMetThrGlyLeuGluArgAspLysLysLysGlnTyrAsnGlu
AATATGACAGGATTAGAAAGAGATAAGAAAAAACAGTATAATGAA

500           *         *         *         *
ThrTrpTyrSerLysAspValValCysGluThrAsnAsnSerThr
ACATGGTACTCAAAAGATGTGGTTTGTGAGACAAATAATAGCACA

*         *         *         *
AsnGlnThrGlnCysTyrMetAsnHisCysAsnThrSerValIle
```

-continued

```
AATCAGACCCAGTGTTACATGAACCATTGCAACACATCAGTCATC

*      600           *         *         *
ThrGluSerCysAspLysHisTyrTrpAspAlaIleArgPheArg
ACAGAATCATGTGACAAGCACTATTGGGATGCTATAAGGTTTAGA

*         *         *         *
TyrCysAlaProProGlyTyrAlaLeuLeuArgCyaAsnAspThr
TACTGTGCACCACCGGGTTATGCCCTATTAAGATGTAATGATACC

*         *       700           *         *
AsnTyrSerGlyPheAlaProAsnCysSerLysValValAlaSer
AATTATTCAGGCTTTGCACCCAACTGTTCTAAAGTAGTAGCTTCT

ThrCysThrArgMetMetGluThrGluThrSerThrTrpPheGly
ACATGCACCAGGATGATGGAAACGCAAACTTCCACATGGTTTGGC

*         *         *       800           *
PheAsnGlyThrArgAlaGluAsnArgThrTyrIleTyrTrpHis
TTTAATGGCACTAGAGCAGAGAATAGAACATATATCTATTGGCAT

*         *         *         *
GlyArgAspAsnArgThrIleIleSerLeuAsnLysTyrTyrAsn
GGCAGAGATAATAGAACTATCATCAGCTTAAACAAATATTATAAT

*         *         *         *       900
LeuSerLeuHisCysLysArgProGlyAsnLysThrValLysGla
CTCAGTTTGCATTGTAAGAGGCCAGGGAATAAGACAGTGAAACAA

*         *         *         *         *
IleMetLeuMetSerGlyHisValPheHisSerHisTyrGlnPro
ATAATGCTTATGTCAGGACATGTGTTTCACTCCCACTACCAGCCG

*         *         *         *         *
IleAsnLysArgProArgGluAlaTrpCysTrpPheLysGlyLys
ATCAATAAAAGACCCAGACAAGCATGGTGCTGGTTCAAAGGCAAA

1000         *         *         *
TrpLysAspAlaMetGluGluValLysThrLeuAlaLysHisPro
TGGAAAGACGCCATGCAGGAGGTGAAGAGCCTTGCAAAACATCCC

*         *         *         *         *
ArgTyrArgGlyThrAsnAspThrArgAsnIleSerPheAlaAla
AGGTATAGAGGAACCAATGACACAAGGAATATTAGCTTTGCAGCG

*     1100            *         *
ProGlyLysGlySerAspProGluValAlaTyrMetTrpThrAsn
CCAGGAAAAGGCTCAGACCCACAAGTAGCATACATGTGGACTAAG

*         *         *         *         *
CysArgGlyGluPheLeuTyrCysAsnMetThrTrpPheLeuAsn
TGCAGAGGAGAGTTTCTCTACTGCAACATGACTTGGTTCCTCAAT

*         *      1200           *
TrpIleGluAsnLysThrHisArgAsnTyrAlaProCysHisIle
TGGATAGAGAATAAGACACACCGCAATTATGCACCGTGCCATATA

*         *         *         *         *
LysGluIleIleAsnThrTrpHisLysValGlyArgAsnValTyr
AAGCAAATAATTAACACATGGCATAAGGTAGGGAGAAATGTATAT

*         *         *     1300
LeuProProArgGluGlyGluLeuSerCysAsnSerThrValThr
TTGCCTCCCAGGGAAGGGGAGCTGTCCTGGAACTCAACAGTAACC

*         *         *         *         *
SerIleIleAlaAsnIleAspTrpGlnAsnAsnAsnGlnThrAsn
AGCATAATTGCTAACATTGACTGGCAAAACAATAATCAGACAAAC

*         *        *         *
IleThrPheSerAlaGluValAlaGluLeuTyrArgLeuGluLeu
ATTACCTTTAGTGCAGAGGTGGCAGAACTATACAGATTGGAGTTG
```

-continued

```
             1400      *        *        *        *
GlyAspTyrLysLeuValGluIleThrProIleGlyPheAlaPro
GGAGATTATAAATTGGTAGAAATAACACCAATTGGCTTCGCACCT

*        *        *        *        *
ThrLysGluLysArgTyrSerSerAlaHisGlyArgHisThrArg
ACAAAAGAAAAAAGATACTCCTCTGCTCACGGGAGACATAGAAGA

*     1500        *        *        *
GlyValPheValLeuGlyPheLeuGlyPheLeuAlaThrAlaGly
GGTGTGTTCGTGCTAGGGTTCTTGGGTTTTCTCGCAACAGCAGGT

*        *        *        *        *
SerAlaMetGlyAlaArgAlaSerLeuThrValSerAlaGluSer
TCTGCAATGGGCGCTCGAGCGTCCCTGACCGTGTCGGCTCAGTGC

*        *     1600        *        *
ArgThrLeuLeuAlaGlyIleValGlnGlnGlnGlnGlnLeuLeu
CGGACTTTACTGGCCGGGATAGTGCAGCAACAGCAACAGCTGTTG

*        *        *        *        *
AspValValLysArgGlnGlnGluLeuLeuArgLeuThrValTrp
GACGTGGTCAAGAGACAACAAGAACTGTTGCGACTGACCGTCTGG

*        *        *        *     1700
GlyThrLysAsaLeuGlnAlaArgValThrAlaIleGluLysTyr
GGAACGAAAAACCTCCAGGCAAGAGTCACTGCTATAGAGAAGTAG

*        *        *        *        *
LeuGlnAspGlnAlaArgLeuAsnSerTrpGlyCysAlaPheArg
CTACAGGACCAGGCGCGGCTAAATTCATGGGGATGTGCGTTTAGA

*        *        *        *        *
GlnValCysHisThrThrValProTrpValAsnAspSerLeuAla
CAAGTCTGCCACACTACTGTACCATGGGTTAATGATTCCTTAGCA

*        *        *        *        *
ProAspTrpAspAsnMetThrTrpGlnGluTrpGluLysGlnVal
CCTGACTGGGACAATATGACGTGGCAGGAATGGGAAAAACAAGTC

*        *        *        *        *
ArgTyrLeuGluAlaAsnIleSerLysSerLeuGluGlnAlaGln
CGCTACCTGGAGGCAAATATCAGTAAAAGTTTAGAACAGGCACAA

1900        *        *        *        *
IleGlnGlnGluLysAsnMetTyrGluLeuGlnLysLeuAsnSer
ATTCAGCAAGAGAAAAATATGTATGAACTACAAAAATTAAATAGC

*        *        *        *        *
TrpAspIlePheGlyAsnTrpPheAspLeuThrSerTrpValLys
TGGGATATTTTTGGCAATTGGTTTGACTTAACCTCCTGGGTCAAG

*     2000        *        *        *
TyrIleGlnTyrGlyValLeuIleIleValAlaValIleAlaLeu
TATATTCAATATGGAGTGCTTATAATAGTAGCAGTAATAGCTTTA

*        *        *        *        *
ArgIleValIleTyrValValGlnMetLeuSerArgLeuArgLys
AGAATAGTGATATATGTAGTACAAATGTTAAGTAGGCTTAGAAAG

*        *     2100        *        *
GlyTyrArgProValPheSerSerProProGlyTyrIleGlu***
GGCTATAGGCCTGTTTTCTCTTCCCCCCGCGGTTATATCCAATAG

*        *        *        *        *
IleHisIleHisLysAspArgGlyGlnProAlaAsnGluGluThr
ATCCATATCCACAAGGACCGGGGACAGCCAGCCAACGAAGAAACA

*        *        *     2200        *
GluGluAspGlyGlySerAsnGlyGlyAspArgTyrTrpProTrp
GAAGAAGACGGTGGAAGCAACGGTGGAGACAGATACTGGCCCTGG

*        *        *        *        *
ProIleAlaTyrIleHisPheLeuIleArgGlnLeuIleArgLeu
GCGATAGCATATATACATTTCCTGATGCGCCAGCTGATTCGCCTC

*        *        *        *        *
LeuThrArgLeuThrSerIleCysArgAspLeuLeuSerArgSer
TTGACCAGACTATACAGCATCTGCAGGGACTTACTATCAAGGAGC

2300        *        *        *        *
```

-continued

```
PheLeuThrLeuGlnLeuIleTyrGlnAsnLeuArgAspTrpLeu
GTCCTGACCCTCCAACTCATCTACCAGAATCTCAGAGACTGGCTG

*        *        *        *        *
ArgLeuArgThrAlaPheLeuGlnTyrGlyCysGluTrpIleGln
AGACTTAGAACAGCCTTCTTGCAATATGGGTGCGAGTGGATCCAA

*     2400        *        *        *
GluAlaPheGlnAlaAlaAlaArgAlaThrArgGluThrLeuAla
GAAGCATTCCAGGCCGCCGCGAGGGCTACAAGAGAGACTCTTGCG

*        *        *        *        *
GlyAlaCysArgGlyLeuTrpArgValLeuGluArgIleGlyArg
GGCGCGTGCAGGGGCTTGTGGAGGGTATTCGAACGAATCGGGAGG

*        *     2500        *        *
GlyIleLeuAlaValProArgArgIleArgGlnGlyAlaGluIle
GGAATACTCGCGGTTCCAAGAAGGATCAGACAGGGCGAAGAAATC

*        *        *        *        *
AlaLeuLeu***GlyThrAlaValSerAlaGlyArgLeuTyrGlu
GGCCTCCTGTGAGGGACGGCAGTATCAGCAGGGAGACTTTATGAA

*        *        *     2600        *
TyrSerMetGluGlyProSerSErArgLysGlyGluLysPheVal
TACTCCATGCAAGGACCCAGCAGCAGAAAGGGAGAAAAATTTGTA

*        *        *        *        *
GlnAlaThrLysTyrGly
CAGGCAACAAAATATGGA
   *

1800 MetGlyAlaArgAsnSerValLeuArgGlyLysLysAlaAspGlu
     ATGGGCGCGAGAAACTCCGTCTTGAGAGGGAAAAAAGCAGATGAA

*        *        *        *        *
LeuGluArgIleArgLeuArgProGlyGlyLysLysLysTyrArg
TTAGAAAGAATCAGGTTACGGCCCGGCGGAAAGAAAAAGTACAGG

*        *        *        *        *
LeuLysHisIleValTrpAlaAlaAsnLysLeuAspArgPheGly
CTAAAACATATTGTGTGGGCAGCGAATAAATTGCACAGATTCGGA

*      100        *        *        *
LeuAlaGluSerLeuLeuGluSerLysGlyCysGluLysIle
TTAGCAGAGAGCCTGTTGGAGTCAAAAGAGGGTTGTCAAAAAATT

*        *        *        *        *
LeuThrValLeuAspProMetValProThrGlySerGluAsnLeu
CTTACAGTTTTAGATCCAATGGTACCGACAGGTTCAGAAAATTTA

*      200        *        *        *
LysSerLeuPheAsnThrValCysValIleTrpCyrIleHisAla
AAAAGTCTTTTTAATACTGTCTGCGTCATTTGGTGCATACAGGCA

*        *        *        *        *
GluGluLysValLysAspThrGluGlyAlaLysGlnIleValArg
GAAGAGAAAGTGAAAGATACTGAAGGAGCAAAACAAATAGTGCGG

*        *      300        *        *
ArgHisLeuValAlaGluThrGlyThrAlaGluLysMetProSer
AGACATCTAGTGGCAGAAACAGGAACTGCAGAGAAAATGCCAAGC

*        *        *        *        *
ThrSerArgProThrAlaProSerSerGluLysGlyGlyAsnTyr
ACAAGTAGACCAACAGCACCATCTAGCGAGAAGGGAGGAAATTAC

*        *        *      400        *
ProValGlnHisValGlyGlyAsnTyrThrHisIleProLeuSer
CCAGTGCAACATGTAGGCGGCAACTACACCCATATACCGCTGAGT

*        *        *        *        *
ProArgThrLeuAsnAlaTrpValLysLeuValGluGluLysLys
CCCCGAACCCTAAATGCCTGGGTAAAATTAGTAGAGGAAAAAAAG

*        *        *        *        *
PheGlyAlaGluValValProGlyPheGlnAlaLeuSerGluGly
TTCGGGGCAGAAGTAGTGCCAGGATTTCAGGCACTCTCAGAAGGC

500        *        *        *        *
```

-continued
```
CysThrProTyrAspIleAsnGlnMetLeuAsnCysValGlyAsp
TGCACGCCCTATGATATCAACCAAATGCTTAATTGTGTGGGCGAC

*         *         *         *         *
HisGlnAlaAlaMetGlnIleIleArgGluIleIleAsnGluGlu
CATCAAGCAGCCATGCAGATAATCAGGGAGATTATCAATGAGGAA

*        600        *         *         *
AlaAlaGluTrpAspValGlnHisProIleProGlyProLeuPro
GCAGCAGAATGGGATGTGCAACATCCAATACCAGGCCCCTTAGCA

*         *         *         *         *
AlaGlyGlnLeuArgGluProArgGlySerAspIleAlaGlyThr
GCGGGGCAGCTTAGAGAGCCAAGGGGATCTGACATAGCAGGGACA

*         *        700        *         *
ThrSerThrValGluGluGlnIleGlnTrpMetPheArgProGlu
ACAAGCACAGTAGAACAACAGATCCAGTGGATGTTTAGGCCACAA

AsnProValProValGlyAsnIleTyrArgArgTrpIleGlnIle
AATCCTGTACCAGTAGGAAACATCTATAGAAGATGGATCCAGATA

*         *         *        800        *
GlyLeuGlnLysCysValArgMetTyrAsnProThrAsnIleLeu
GGATTGCAGAAGTGTGTCAGGATGTAGAACCCGACCAACATCCTA

*         *         *         *         *
AspIleLysGlnGlyProLysGluProPheGlnSerTyrValAsp
GACATAAAACAGGGACCAAAGGAGCCGTTCCAAAGCTATGTAGAT

*         *         *         *        900
ArgPheTyrLysSerLeuArgAlaGluGlnThrAspProAlaVal
AGATTCTACAAAAGCTTGAGGGCAGAACAAACAGATCCAGCAGTG

*         *         *         *         *
LysAsnTrpMetThrGlnThrLeuLeuValGlnAsnAlaAsnPro
AAGAATTGGATGACCCAAACACTGCTAGTACAAAATGCCAACCCA

*         *         *         *         *
AspCysLysLeuValLeuLysGlyLeuGlyMetAsnProThrLeu
GACTGTAAATTAGTGCTAAAAGGACTAGGGATGAACCCTACCTTA
   1000       *         *         *         *
GluGluMetLeuThrAlaCysGlnGlyValGlyGlyProGlyGln
GAAGAGATGCTGACCGCCTGTCAGGGGGTAGGTGCGCCAGGCCAG

*         *         *         *         *
LysAlaArgLeuMetAlaGluAlaLeuLysGluValIleGlyPro
AAAGCTAGATTAATGGCAGAGGCCCTGAAAGAGGTCATAGGACCT

*       1100        *         *         
AlaProIleProPheAlaAlaAlaGlnGlnArgLysAlaPheLys
GCCCCTATCCCATTCGCAGCAGCCCAGCAGAGAAAGGCATTTAAA

*         *         *         *         *
CysTrpAsnCysGlyLysGluGlyHisSerAlaArgGlnCysArg
TGCTGGAACTGTGGAAAGGAAGGGCACTCGGCAAGACAATGCCGA

*         *       1200        *         
AlaProArgArgGlnGlyCysTrpLysCysGlyLysProGlyHis
GCACCTAGAAGGCAGGGCTGCTGGAAGTGTGGTAAGCCAGGACAC

*         *         *         *         *
IleMetThrAsnCysProAspArgGlnAlaGlyPheLeuGlyLeu
ATCATGACAAACTGCCCAGATAGACAGGCAGGTTTTTTAGGACTG

*         *         *       1300        
GlyProTrpGlyLysLysProArgAsnPheProValAlaGlnVal
GGCCCTTGGGGAAAGAAGCCCCGCAACTTCCCCGTGGCCCAAGTT

*         *         *         *         *
ProGlnGlyLeuThrProThrAlaProProValAspProAlaVal
CCGCAGGGGCTCACACCAACAGCACCCCCAGTGGATCCAGCAGTG

*         *         *         *         *
AspLeuLeuGluLysTyrMetGlnGlnGlyLysArgGlnArgGlu
GATCTACTGGAGAAATATATGCAGCAAGCGAAAAGACAGACAGAG
  1400        *         *         *         *
GlnArgGluArgProTyrLysGluValThrGluAspLeuLeuHis
CAGAGAGAGAGACCATACAAGGAAGTGACAGAGGACTTACTGCAC
```

-continued
```
    *         *         *         *         *
LeuGluGlnGlyGluThrProTyrArgGluProProThrGluAsp
CTCGAGCAGGGGGAGACACCATACAGGGAGCCACCAACAGAGGAC

*       1500        *         *         *
LeuLeuHisLeuAsnSerLeuPheGlyLysAspGln
TTGCTGCACCTCAATTCTCTCTTTGGAAAAGACCAG
    *         *         *
```

Example 6

Peptide Sequences Encoded By The ENV and GAG Qenes

The following coding regions for antigenic peptides, identified for convenience only by the nucleotide numbers of Example 5, within the env and gag gene regions are of particular interest.

```
env1 (1732-1809)

ArgValThrAlaIleGluLysTyr
                        AGAGTCACTGCTATAGAGAAGTAC
LeuGlnAspGlnAlaArgLeuAsnSerTrpGlyCysAlaPheArg
CTACAGGACCAGGCGCGGCTAAATTCATGGGGATGTGCGTTTAGA
    *         *         *         *      1000
GlnValCys
CAAGTCTGC env2 (1912-1983)

SerLysSerLeuGluGlnAlaGln
                        AGTAAAAGTTTAGAACAGGCACAA
                              *         *
IleGlnGlnGluLysAsnMetTyrGluLeuGlnLysLeuAsnSer
ATTCAGCAAGAGAAAAATATGTATGAACTACAAAAATTAAATAGC
 1940         *         *         *         *
Trp
TGG env3 (1482-1530)

Pro ThrLysGluLysArgTyrSerSerAla-
HisGlyArgHisThrArg
CCT ACAAAAGAAAAAAGATACTCCTCTGCT-
CACGGCAGACATACAAGA
            *       1500        *         *         * env4 (55-129)

CysThrGlnTyrValThrValPheTyrGlyValPro
        TGCACCCAATATGTAACTGTTTTCTATGGCGTACCC
    *         *         *         *         *
ThrTrpLysAsnAlaThrIleProLeuPheCysAlaThr
ACGTGGAAAAATGCAACCATTCCCCTGTTTTGTGCAACC
        100       *         * env5 (175-231)

AspAsp
                                          GATGAT
                                          *
TyrGlnGluIleThrLeuAsnValThrGluAlaPheAspAlaTrp
TATCAGGAAATAACTTTTGAATGTAACAGAGGCTTTTGATGCATGG
    *       200        *         *
AsnAsn
AATAAT env6 (274-330)

GluThrSerIleLysProCysValLysLeuThrProLeuCys
    GAGACATCAATAAAACCATGTGTCAAACTAACACCTTTATGT
        *         *      300        *
ValAlaMetLysCys
GTAGCAATGAAATGC
```

-continued

```
env7 (607-660)

AsnHisCysAsnThrSerValIle
                        AACCATTGCAACACATCAGTCATC
                        610           *       *
ThrGluSerCysAspLysHisTyrTrpAsp
ACAGAATCATGTGACAAGCACTATTGGAT
    *           *           * env8 (661-720)

AlaIleArgPheArg
                              GCTATAAGGTTTAGA
                                    *
TyrCysAlaProProGlyTyrAlaLeuLeuArgCysAsnAspThr
TACTGTGCACCACCGGGTTATGCCCTATTAAGATGTAATGATACC
   *        *        700         *        * env9 (997-1044)

LysArgProArgGlnAlaTrpCysTrpPheLysGlyLys
    AAAAGACCCAGACAAGCATGGTGCTGGTTCAAAGGCAAA
    1000           *           *           *
TrpLysAsp
TGGAAAGAC env10 (1132-1215)

LysGlySerAspProGluValAlaTyrMetTrpThrAsn
    AAAGGCTCAGACCCAGAAGTAGCATACATGTGGACTAAG
         *           *         *         *
CysArgGlyGluPheLeuTyrCysAsnMetThrTrpPheLeuAsn
TGCAGAGGAGAGTTTCTCTACTGCAACATGACTTGGTTCCTCAAT
    *              *      1200          * env11 (1237-1305)

ArgAsnTyrAlaProCysHisIle
                     CGCAATTATGCACCGTGCCATATA
                        *           *        *
LysGlnIleIleAsnThrTrpHisLysValGlyArgAsnValTyr
AAGCAAATAATTAACACATGGCATAAGGTAGGGAGAAATGTATAT
      *          *           *           1300 gag1 (991-1053)

AspCysLysLeuValLeuLysGlyLeuGlyMetAsnProThrLeu
GACTGTAAATTAGTGCTAAAAGGACTAGGGATGAACCCTACCTTA
         1000        *          *         *
GluGluMetLeuThrAla
GAAGAGATGCTGACCGCC
        *          *
```

Of the foregoing peptides, env1, env2, env3 and gag1 are particularly contemplated for diagnostic purposes, and env4, env5, env6, env7, env8, env9, env10 and env11 are particularly contemplated as protecting agents. These peptides have been selected in part because of their sequence homology to certain of the envelope and gag protein products of other of the retroviruses in the H6V group. For vaccinating purposes, the foregoing peptides may be coupled to a carrier protein by utilizing suitable and well known techniques to enhance the host's immune response. Adjuvants such as calcium phosphate or alum hydroxide may also be added. The foregoing peptides can be synthesized by conventional protein synthesis techniques, such as that of Merrifield.

It will be apparent to those skilled in the art that various modifications and variations can be made in the processes and products of the present invention. Thus, it is intended that the present application cover the modifications and variations of this invention provided they come within the scope of the appended claims and their equivalents. For convenience in interpreting the following claims, the following table sets forth the correspondence between codon codes and amino acids and the correspondence between three-letter and one-letter amino acid symbols.

| | | DNA CODON | | | AMINO ACID 3 LET. | | | AMINO ACID 1 LET. | | |
|---|---|---|---|---|---|---|---|---|---|---|
| | \2 | T | C | A | G | T | C | A | G | T C A G |
| 1 | \3 | | | | | | | | | |
| T | T | TTT | TCT | TAT | TGT | PHE | SER | TYR | CYS | F S Y C |
| T | C | TTC | TCC | TAC | TGC | PHE | SER | TYR | CYS | F S Y C |
| | A | TTA | TCA | TAA | TGA | LEU | SER | *** | *** | L S * * |
| | G | TTG | TCG | TAG | TGG | LEU | SER | *** | TRP | L S * N |
| | T | CTT | CCT | CAT | CGT | LEU | PRO | HIS | ARG | L P H R |
| C | C | CTC | TCC | TAC | TGC | LEU | PRO | HIS | ARG | L P H R |
| | A | CTA | CCA | CAA | CGA | LEU | PRO | GLN | ARG | L P Q R |
| | G | CTG | CCG | CAG | CGG | LEU | PRO | GLN | ARG | L P Q R |
| | T | ATT | ACT | AAT | AGT | ILE | THR | ASN | SER | I T N S |
| A | C | ATC | ACC | AAC | AGC | ILE | THR | ASN | SER | I T N S |
| | A | ATA | ACA | AAA | AGA | ILE | THR | LYS | ARG | I T K R |
| | G | ATG | ACG | AAG | AGG | ILE | THR | LYS | ARG | M T K R |
| | T | GTT | GCT | GAT | GGT | VAL | ALA | ASP | GLY | V A D G |
| G | C | GTC | GCC | GAC | GGC | VAL | ALA | ASP | GLY | V A D G |
| | A | GTA | GCA | GAA | CGA | VAL | ALA | GLU | GLY | V A E G |
| | G | GTG | GCG | GAG | GGG | VAL | ALA | GLU | GLY | V A E G |

| 3 Letter | 1 Letter | CODONS |
|---|---|---|
| ALA | A | GCT GCC GCA GCG |
| ARG | R | CGT CGC CGA CGC AGA AGG |
| ASN | N | AAT AAC |
| ASP | D | GAT GAC |
| CYS | C | TGT TGC |
| GLN | D | CAA CAG |
| GLU | E | GAA GAG |
| GLY | G | GGT GGC GGA GGG |
| HIS | H | CAT CAC |
| ILE | I | ATT ATC ATA |
| LEU | L | CTT CTC CTA CTG TTA TTG |
| LYS | K | AAA AAG |
| MET | M | ATG |
| PHE | F | TTT TTC |
| PRO | P | CCT CCC CCA CCG |
| SER | S | TCT TCC TCA TCG AGT AGC |
| THR | R | ACT ACC ACA ACG |
| TRP | W | TGG |
| TYR | Y | TAT TAC |
| VAL | V | GTT GTC GTA GTG |
| *** | * | TAA TAG TGA |

What is claimed is:

1. A peptide comprising an amino acid sequence selected from the group consisting of CAFRQVC.

2. A polypeptide conjugate comprising the peptide of claim 1 linked to a carrier.

3. An antigenic composition comprising the peptide of claim 1.

4. The antigenic composition of claim 3, wherein the peptide specifically binds to an anti-retroviral antibody selected from the group consisting of anti-HIV-1 and anti-HIV-2 antibodies.

5. An antigenic composition comprising the polypeptide conjugate of claim 2 and a pharmaceutically acceptable vehicle.

6. An in vitro method of detecting antibodies selectively binding to a retrovirus selected from the group consisting of HIV-1 and HIV-2 in a biological sample, comprising
    contacting a biological sample suspected of comprising an antibody having specificity for a retrovirus selected from the group consisting of HIV-1 and HIV-2 with the peptide of claim 1, a conjugate thereof with a carrier, or a mixture thereof, and
    detecting any peptide-antibody or conjugate-antibody complexes formed.

7. The in vitro method of claim 6, wherein the detection of the peptide-antibody or conjugate-antibody complexes formed is carried out by an immunoenzymatic, immunofluorescence, radioimmunological, or radioimmunoprecipitation assay.

8. A kit for the in vitro detection of antibodies selectively binding to a retrovirus selected from the group consisting of the HIV-1 and HIV-2 viruses comprising in separate containers
- a composition comprising the peptide of claim 1, a conjugate thereof with a carrier, or a mixture thereof;
- at least one first reagent for the preparation of a medium suitable for carrying out an immunological reaction with the composition;
- at least one further reagent for the detection of antigen-antibody complexes formed during an immunological reaction; and
- at least one reference sample comprising a known quantity of antibodies capable of specifically binding to the composition but free of any other antibodies.

9. The peptide of claim 1, wherein the peptide has 40 or less amino acid residues.

10. A polypeptide conjugate comprising the peptide of claim 9 being linked to a carrier.

11. An antigenic composition comprising the peptide of claim 9 or mixtures thereof.

12. The antigenic composition of claim 11, wherein the peptide specifically binds to an anti-retroviral antibody selected from the group consisting of anti-HIV-1 and anti-HIV-2 antibodies.

13. An antigenic composition comprising the polypeptide conjugate of claim 12 and a pharmaceutically acceptable vehicle.

14. An in vitro method of detecting antibodies selectively binding to a retrovirus selected from the group consisting of HIV-1 and HIV-2 in a biological sample, comprising
- contacting a biological sample suspected of comprising an antibody having specificity for a retrovirus selected from the group consisting of HIV-1 and HIV-2 with the peptide of claim 9, a conjugate thereof with a carrier, or a mixture thereof, and
- detecting any peptide-antibody or conjugate-antibody complexes formed.

15. The in vitro method of claim 14, wherein the detection of the peptide-antibody or conjugate-antibody complexes formed is carried out by an immunoenzymatic, immunofluorescence, radioimmunological, or radioimmunoprecipitation assay.

16. A kit for the in vitro detection of antibodies selectively binding to a retrovirus selected from the group consisting of the HIV-1 and HIV-2 viruses comprising in separate containers
- a composition comprising the peptide of claim 9, a conjugate thereof with a carrier, or a mixture thereof;
- at least one first reagent for the preparation of a medium suitable for carrying out an immunological reaction with the composition;
- at least one further reagent for the detection of antigen-antibody complexes formed during an immunological reaction; and
- at least one reference sample comprising a known quantity of antibodies capable of specifically binding to the composition but free of any other antibodies.

* * * * *

UNITED STATES PATENT AND TRADEMARK OFFICE
CERTIFICATE OF CORRECTION

PATENT NO. : 6,518,015 B1
DATED : February 11, 2003
INVENTOR(S) : Marc Alizon et al.

It is certified that error appears in the above-identified patent and that said Letters Patent is hereby corrected as shown below:

<u>Title page,</u>
Item [75], Inventors, "Denise G Guétard," should read -- Denise Guétard, --.

Signed and Sealed this

Tenth Day of June, 2003

JAMES E. ROGAN
*Director of the United States Patent and Trademark Office*